(12) United States Patent
Wei

(10) Patent No.: US 11,389,397 B2
(45) Date of Patent: *Jul. 19, 2022

(54) METHOD TO REDUCE FACE MASK AND RESPIRATOR DISCOMFORT

(71) Applicant: Edward Tak Wei, Berkeley, CA (US)

(72) Inventor: Edward Tak Wei, Berkeley, CA (US)

(*) Notice: Subject to any disclaimer, the term of this patent is extended or adjusted under 35 U.S.C. 154(b) by 215 days.

This patent is subject to a terminal disclaimer.

(21) Appl. No.: 16/873,767

(22) Filed: Jun. 29, 2020

(65) Prior Publication Data

US 2021/0361564 A1 Nov. 25, 2021

Related U.S. Application Data

(63) Continuation-in-part of application No. 16/873,626, filed on May 21, 2020.

(51) Int. Cl.
| | |
|---|---|
| A61K 31/66 | (2006.01) |
| A61P 43/00 | (2006.01) |
| A61P 17/00 | (2006.01) |
| A61K 9/00 | (2006.01) |
| A61K 9/06 | (2006.01) |
| A61K 9/08 | (2006.01) |
| A61K 47/32 | (2006.01) |
| A62B 23/02 | (2006.01) |

(52) U.S. Cl.
CPC .......... *A61K 9/0043* (2013.01); *A61K 9/0014* (2013.01); *A61K 9/06* (2013.01); *A61K 9/08* (2013.01); *A61K 31/66* (2013.01); *A61K 47/32* (2013.01); *A62B 23/025* (2013.01)

(58) Field of Classification Search
None
See application file for complete search history.

(56) References Cited

U.S. PATENT DOCUMENTS

| | | | | |
|---|---|---|---|---|
| 4,070,496 | A * | 1/1978 | Rowsell | A23L 27/202 424/602 |
| 6,893,626 | B2 * | 5/2005 | Wei | A61K 51/02 424/1.81 |
| 8,529,915 | B2 * | 9/2013 | Wei | A61K 31/215 514/738 |
| 9,642,868 | B2 * | 5/2017 | Wei | A61K 47/02 |
| 9,895,382 | B2 * | 2/2018 | Wei | A61K 49/00 |
| 10,195,217 | B2 * | 2/2019 | Wei | A61P 11/02 |
| 10,722,477 | B2 * | 7/2020 | Wei | A61K 31/66 |
| 2015/0111852 | A1 * | 4/2015 | Wei | A61P 43/00 514/75 |
| 2015/0164924 | A1 * | 6/2015 | Wei | A61P 17/00 424/443 |
| 2019/0105335 | A1 * | 4/2019 | Wei | A61K 9/0014 |

* cited by examiner

*Primary Examiner* — Bethany P Barham
*Assistant Examiner* — Peter Anthopolos

(57) ABSTRACT

Wearing a face mask or a filtering facepiece respirator, especially in hot weather for more than one hour, causes discomfort. But, in a viral pandemic, a barrier to filter inhaled and exhaled air is necessary to protect against airborne pathogens. The sensations of heat abstraction, that is, coolness and cold, can be captured by the rational design of optimized molecules called TRPM8 receptor agonists. The topical application of these molecules alleviates the discomfort of wearing a face mask covering. Several entities were identified by synthesis and experiment as having the ideal properties for achieving this purpose. The preferred embodiments are certain 1-diisopropyl-phosphinoyl-alkanes described as DIPA-1-5, DIPA-1-6, DIPA-1-7, DIPA-1-8, and DIPA-1-9, collectively referred to herein as "DIPA compounds." The applicant found that topical delivery of DIPA compounds to the facial skin, especially to the surface of the nares (nostrils), alleviates face mask discomfort. From these studies, it is hypothesized that it is the absence of cool air dynamics about the nostrils that causes face mask discomfort. The present discovery pertains to pharmaceutical compositions that relieve face mask discomfort.

11 Claims, 13 Drawing Sheets

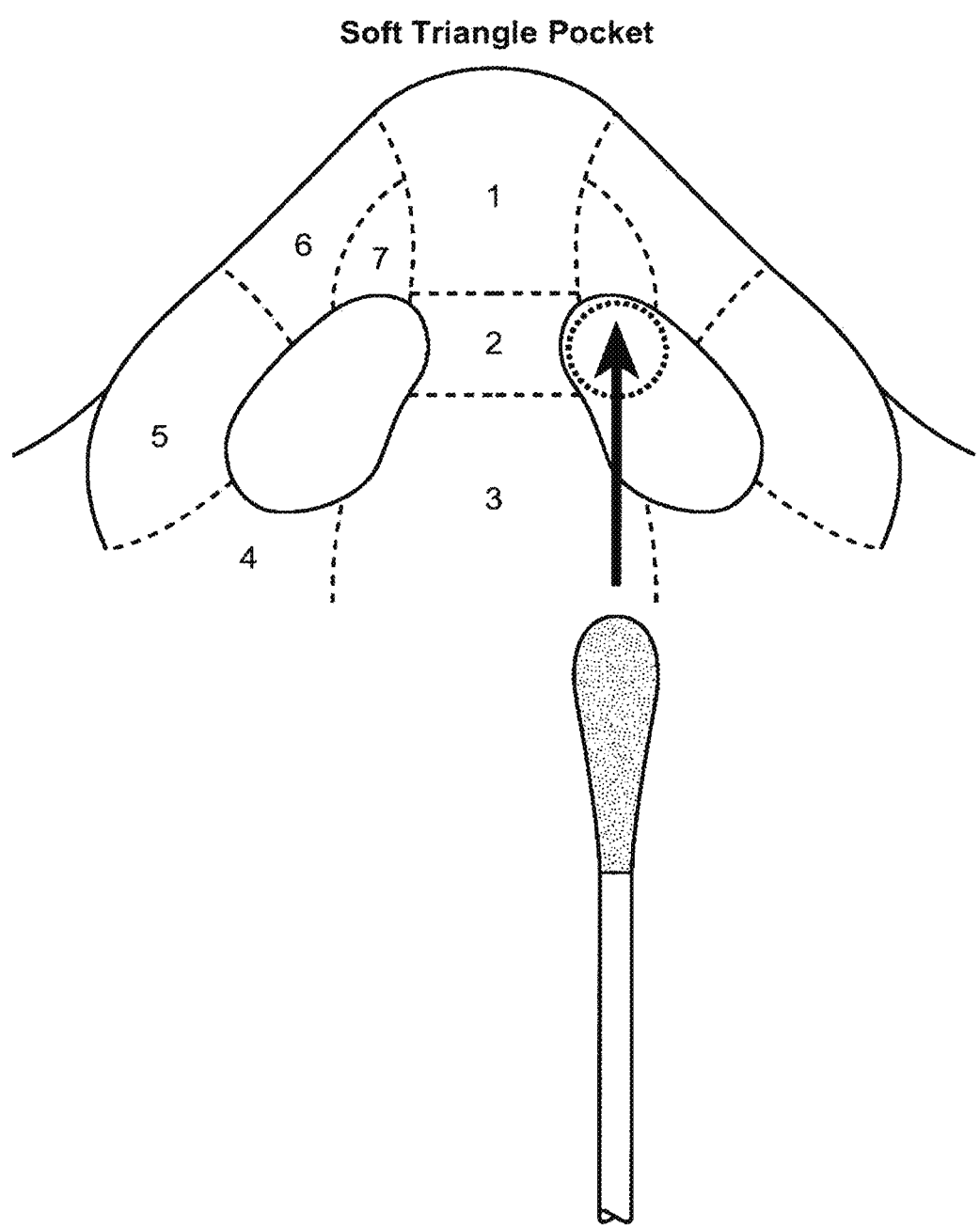

METHOD TO REDUCE FACE MASK AND RESPIRATOR DISCOMFORT

CROSS-REFERENCE TO RELATED APPLICATIONS

This application is a continuation-in-part to U.S. Ser. No. 16/873,626 filed May 21, 2020.

BACKGROUND OF THE INVENTION

Respiratory tract infections caused by microorganisms such as viruses and bacteria are frequent events. The resultant diseases include sore throat, acute bronchitis, the common cold, and influenza. Infections of the nose, sinuses, pharynx, larynx, and the large airways are generally self-limiting, with irritation and inflammation, but are seldom life-threatening. The relatively benign viral pathogens are rhinovirus, influenza virus, adenovirus, enterovirus, and respiratory syncytial virus. About 15% of bacterial pharyngitis is due to Streptococcus pyogenes. Respiratory pathogens create a substantial economic burden on society but are considered an acceptable fact of life. By contrast, the new SARS-CoV-2 virus (abbreviated here as CoV-2), the causative agent of the coronavirus pandemic of 2019+ (COVID-19) is a severe threat to humankind because of rapid contagion, increased morbidity, and mortality, and extreme patient suffering.

One consequence of this pandemic is the need to wear a facial covering to prevent CoV inspiration or to reduce CoV expiration from an infected person. But the wearing of masks, especially the tight-fitting ones called N95 filtering facepiece respirators (N95-FFR), for periods of longer than one hour are uncomfortable, especially in hot weather. The technology here addresses the problem of mask and respirator discomfort [NIOSH, 2015. Workplace solutions: preparedness through daily practice: the myths of respiratory protection in healthcare. Krah J et al., Cincinnati, Ohio].

Pathogenesis of Airborne Transmission and the Need for Masks

Coronaviruses (CoV), a subfamily of Coronavirida, are RNA viruses with genomes of ~30 Kb. Of the seven known human coronaviruses, four cause mild symptoms such as nasal congestion and cough. The dangerous CoV are β-CoV, namely, MERS, SARS-1, and SARS-2 (CoV-2), which attack the lower respiratory tract (LRT) and cause pneumonia.

"Tropism" describes how a virus selectively contacts its host cell via an attachment receptor. The point of contact is an essential determinant of disease infectivity, virulence, and pathogenicity. The viral tropism for β-CoV is attachment to a protein cell membrane receptor called the ACE-2 receptor (for an angiotensin-converting enzyme, type 2) [Hoffmann, M. et al., 2020. "The Novel Coronavirus 2019 (2019-NCoV) Uses the SARS-Coronavirus Receptor ACE2 and the Cellular Protease TMPRSS2 for Entry into Target Cells." BioRxiv, 2020.01.31.929042]. The virus recognizes ACE-2R on host cells via its S-spike proteins, and it is the anatomical distribution of ACE-2R that decides the sites of infection and pathogenesis. After infection and propagation, the next generation of virions emerge from the host cell, like a bunch of frog eggs, and cause havoc.

Anatomically, the boundary of the upper respiratory tract (URT) and LRT is at the glottis. The conducting airways of the LRT have on its luminal surface epithelium and goblet cells and sub-divide for 20 to 22 generations to become the gas exchange surface know as the alveolus (pl. alveoli). The alveoli contain Type 1 (AT1) and Type 2 (AT2) pneumocytes. AT1 cells are flat and allow gas exchange between alveolar air and the pulmonary capillaries. AT2 cells, which are ~2.5% of the total cell's in the alveolus, are cuboidal and synthesize surfactant, a material that prevents the alveoli from collapsing. The host molecule and binding partner of the β-CoV for the virus are angiotensin-converting enzyme-2 (ACE-2R). The S-spike protein of CoV binds to ACE-2R, fuses with the cell membrane, and enters the AT2.

Once the virus enters the AT2 cell, it utilizes the cell's machinery and replicates itself. At some point, the AT2 disintegrates and releases the virions. The outpourings of new virions are abundant. Immune cells, such as macrophages and neutrophils, recognize the foreign virions and release cytokines to begin an attack on the invaders. The resulting "cytokine storm" causes alveolar destruction, loss of oxygen exchange, tissue damage, pneumonia, and fever. In highly susceptible individuals, these events can be explosive, and the infected person can die within five days. Pneumonia accounts for the high morbidity and mortality rates seen with the β-CoV.

The CoV has a long journey through 20+ generations of airways to reach the ACE-2 receptor on AT2 cells. A direct route for the virions to reach target is via droplets that remain suspended in air and gets inhaled deeply to reach the alveoli. These droplet diameters are ≤10 microns (μm). The virus itself has a diameter of about 0.5 μm, but it exists in the air as an aerosol (liquid plus solid), so the bioaerosol has a greater diameter. The human eye can detect particles of about 30 μm, but the small inhalable CoV-2 particles are not visible. The CoV-2 can also move downward from the conducting airways in the alveolar lining fluids (ALF) to the alveoli, but the mucociliary clearance mechanism brushes the ALF upwards towards the larynx. From swab tests for CoV-2, we know that CoV-2 is present in the nasal cavity and on the throat. Incubation of the virus in the URT may generate significant quantities of CoV-2 to overwhelm mucociliary clearance and gain access to the AT2.

The mode of transmission of CoV-2, close-range aerosol spread, dictates the imperative use of masks, or facial covering, as a barrier to prevent infection.

Personal Protection Equipment, Principal Types of Masks

CoV-2 is a contagious pathogen, and healthcare workers (HCW) have succumbed to this virus. The factors that contribute to increased risk, such as long hours of close contact in the ICU, require wearing a well-fitted N95-facial filtration respirator (FFR) type of mask together with a protective gown (FIG. 1). Alternative procedures for protection from infection include physical (social) distancing, cough etiquette, and handwashing but are not effective for close patient contact (<3 feet) [Nicas et al., Relative Contributions of four exposure pathways to influenza infection risk. Risk Anal., 2009]. "Personal protective equipment" (PPE), which includes respirators, face masks, gloves,[3] eye protection, face shields, gowns, and head and shoe coverings, are physical interventions to prevent the entry of CoV into the body. For the airways, respirators are designed to purify or filter inhaled air. N95 (95% efficiency) filtering-facepiece respirators (N95-FFR) are manufactured from electrostatic filter material such as polypropylene, which yield high collection efficiency due to electrostatic attraction of charge particles and low breathing resistance. By contrast, face masks (FM), also called surgical masks, are loose-fitting coverings made from fabric and designed to protect the patient from secretions from the nose and mouth of the HCW. Face masks are not designed to protect the wearer from exposure to respiratory hazards but do have some value as barriers to penetration of pathogens into the wearer. For healthcare personnel in close contact (defined <3 feet) with symptomatic patients, PPE is N95 (95% efficiency) filtering-facepiece respirators (N95-FFR), safety eyeglasses, and disposable clothing. These methods of protection [National Academies Press. Reusability of facemasks during an influenza pandemic: facing the flu. Chpt. 2. Characteristics of respirators and medical masks. NAP.edu/10766. Washington, D.C. 20001] follow the postulated pathways for viral transmission. Reduced exposure via the respiratory route of exposure has the highest priority.

Face masks (FM), also called surgical or medical masks, are designed to prevent the wearer's release of large droplets into the environment. FM do not protect much from small particulates (i.e., droplet nuclei) that can harbor pathogens But, it protects HCW from large-droplet splashes or sprays of bodily fluids from patients. FM are typically disposable and loose-fitting, do not form a tight seal to the face, or capture small particles efficiently. By contrast, N95-FFR filter at least 95% of a wide size-range of particles and must be N95-FFR custom-fitted for the wearer. N95-FFR are named where "N" stands for not oil resistant and to be used for oil-free atmospheres. The N95-FFR is for the hospital rooms where there is a high risk of pathogen transmission. In the past 40 years, the dominant N95-FFR is a filtration piece made of non-woven materials such as polypropylene, The N95-FFR removes ~95% of particles, down to a particle size of 0.3μ. N95-FFR, because of its tight fit to the face, may cause skin irritation, a buildup of facial heat, and an increase in airflow resistance. Prolonged and continual use, e.g., >4 hr is not well-tolerated and may lead to a failure of compliance or adherence of use.

A third type of respirator is elastomeric respirators (ER), which are tight-fitting respirators where the facepieces are made of synthetic or natural rubber material and can be repeatedly used, cleaned, disinfected, stored, and re-used. These are alternatives to disposable FM and filtering facepiece respirators (FFR), such as N95 FFR. The ER provides equivalent protection to N95-FFR, and some types of ER offer higher assigned protection factors than N95 FFR. The ER has replaceable filter cartridges or flexible, disc, or pancake-style filters. All ER equipped with the proper air-purification filters, cartridges, or canisters have utility in personal protection. Elastomerics may also have sealing surfaces and adjustable straps that accommodate a better fit. The limits of ER is the expense and re-usability.

Li et al. [2005. Effects of wearing N95 and surgical facemasks on heart rate, thermal stress, and subjective sensations. Int Arch Occup Environ Health; 78:501-9] compared FM and N95-FFR in healthy subjects working at controlled temperature and humidity. After ~80+ min, subjects wearing the N95-FFR started to complain of excess heat and humidity and increased breathing resistance. There was an increase in heart rate and blood pressure, indicative of stress and sympathetic nervous system activation. The N95-FFR subjects felt unfit, fatigued, and complained of overall discomfort. This evidence of heat stress from N95-FFR masks is manifest in clinical environments, e.g., in the Emergency Departments of hospitals treating CoV infections. Farquharson reported that working 12-h shifts while wearing an N95-FFR mask was a serious challenge to their staff [2003. "Responding to the Severe Acute Respiratory Syndrome (SARS) Outbreak: Lessons Learned in a Toronto Emergency Department." J. Emergency Nursing 29 (3): 222-28].

Effectiveness of Masks and PPE

Tracht et al. [2010. "Mathematical Modeling of the Effectiveness of Facemasks in Reducing the Spread of Novel Influenza a (H1N1)." PLoS ONE 5 (2)] modeled the effectiveness of FM and N95-FFR in reducing the spread of influenza for 2009 H1N1. He estimated that when masks or respirators were absent, the infected population was 75%; if 10% wore FM, the percentage infected was 73%; if 50% wore FM, the infected population was 69%. By contrast, if 10% wore N95-FRR, the infected was 55%; and if 50% wore N95-FFR, they would drop to 0.1%. These results are speculative and not proven by an experiment.

In a more direct study of effectiveness, MacIntyre et al. [A randomized clinical trial of three options for N95 respirators and medical masks for clinical health workers. Amer. J Critical Respiratory Care. 187, 960-966, 2013] compared the use of facial coverings in 14 hospitals. HCW were put into groups of FM, continuous use of N95-FFR, or targeted use of N95-FFR (while doing high-risk procedures or barrier nursing). Outcomes were clinical respiratory illness (CRI). The results showed CRI was highest in the FM group (17%), followed by the targeted N95 arm (11.8%), and lowest in the continuous N95 arm (7.2%) ($P<0.05$). MacIntyre concluded that N95-FFR was more efficacious against CRI than intermittent use of N95-FFR or medical masks.

The use of personal protective equipment and history of high-risk patient care activities among SARS-exposed nurses [Loeb et al. 2004. "SARS among Critical Care Nurses, Toronto." Emerging Infectious Diseases 10 (2): 251-55] found that three (13%) of 23 nurses who consistently wore a mask (either surgical or N95-FFR) acquired SARS compared to 5 (56%) of 9 nurses who did not consistently wear a mask. The relative risk (RR) for infection was 0.22 and statistically significant, $p=0.06$.

Sensory Events on the Facial Areas Covered by a Mask and Mask Discomfort

A standard N95-FFR mask covers the skin over the bridge of the nose, the cheeks, the mouth, and the chin. The areas enclosed by the nasolabial folds (smile lines), alar crease, the nostrils, vermilion, and the lower lip, are sensitive to heat. The skin of the nares and vestibule epithelium sense airflow, temperature and humidity. In the respiratory epithelium, within the nasal cavity, receptive fields are present, especially around Kiesselbach's plexus (Little's area). The cranial nerves transmit somatosensory and thermosensory signals from the face, nasal cavity, and mouth. These signals are highly integrated into temperature regulation, as exemplified by the observation that cooling of the face is two to five times more effective at suppressing sweating and thermal discomfort than cooling an equivalent skin area elsewhere on the body [Cotter JD, Taylor NA. (2005). The distribution of cutaneous sudomotor and alliesthesial thermosensitivity in mildly heat-stressed humans: an open-loop approach. J Physiol; 565: 335-45].

Reasons for Face Mask Discomfort

Roberge et al. [2012. "Protective Facemask Impact on Human Thermoregulation: An Overview." *Annals of Occupational Hygiene* 56 (1): 102-12] reviewed the postulated reasons for FM and FFR discomfort. Factors considered were respiratory heat exchange mechanisms, the pathways of heat gain and loss from the nose and mouth, the thermoload of protective facemasks, facial skin temperature, dead space heat and humidity, and psychophysiological heat responses. No conclusions were reached on the best strategy to reduce discomfort. Suggested mitigation measures were refrigeration of masks, miniature-battery powered fans, altering the geometry of masks, and exhalation valves to reduce heat accumulation. Only exhalation valves have reached the market, but the benefits appear limited. The valves add to the respirator's expense and are banned if the wearer's exhalation is likely to infect others. The pharmacological treatment of the mask discomfort has not been contemplated.

In summary, the inhalation of a β-CoV is an urgent worldwide threat to health. The interposition of a barrier, in the form of a mask (FM or N-95-FFR), has a protective function of filtration. In a pandemic, the benefits of wearing a facial cover by HCW are overwhelming and self-evident. The use of masks is now ubiquitous, but sensory discomfort from a mask is a hindrance to continued and adherent use.

BRIEF SUMMARY OF THE INVENTION

The CoV pandemic of 2019+ has increased the need for efficient use of personal protection equipment (PPE), as the number of sick exponentially increases. A necessary part of protection is a mask filter barrier to prevent the entry and exit of the virion from the nose and mouth of the wearer. A mask barrier reduces respiratory transmission, the most dangerous route of viral infection. Inhaled virions reach their host cell in the alveoli via the conducting airways. Preventing the entry of inhaled particles is an established method of protection. In the hospital, especially in intensive care units, health care workers (HCW) must wear tight-fitting masks for long hours, sometimes wearing impermeable gowns which adds to the heat load. The resulting sensory discomfort leads to non-adherence to the use of masks and an increased risk of infection. A method to reduce sensory discomfort from wearing a mask has value.

Wearing a facial covering is an artificial and unnatural event, but now frequent because of the pandemic. A face mask (FM) or an N95-FFR (filtering facepiece respirator) covers a defined region of the face, which includes the cheeks, and the nasal and perioral areas. But a facial covering is a barrier to air exchange. Heat and water vapor accumulates behind the mask and acts on thermosensors and mechanoreceptors. But what are the precise anatomical sites and mechanisms of mask discomfort?

In the laboratory and field studies, the descriptions of sensory discomfort of masks give a list of signs and symptoms. Subjects wearing fitted N95 respirators complain of increased resistance to airflow when breathing. Then, there are complaints of heat buildup and increased humidity behind the mask, especially in a hot environment. Then there are complaints of loss of concentration, perceptual disorientation, headache, lightheadedness, and impeded communication [Rebmann et al. 2013. "Physiologic and Other Effects and Compliance with Long-Term Respirator Use among Medical Intensive Care Unit Nurses." American Journal of Infection Control 41 (12): 1218-23]. Somatic complaints are of an increased heart rate, shortness of breath, skin irritation, and feelings of nausea. These complaints increase with the duration of continuous use, beginning in one laboratory study after 80 min. Most wearers find work-shift durations of 4 hr, 8 hr, and 12 hr to be unpleasant. In an infected area, however, protocols for the removal of a mask are strict, laborious, and tedious, so masks are mandatory. A postulated correlation of ambient temperature to mask discomfort is shown in FIG. 2.

To ascertain the precise anatomical sites and mechanisms of discomfort, experiments were conducted. A cooling agent, called a TRPM8 agonist, was topically applied to different sites of the face of volunteers to determine the site that best counteracts the discomfort caused by wearing an N95 FFR for 1 to 1.5 hr. A TRPM8 agonist skin gel containing 1.5% (15 mg/mL) of DIPA-1-7 was applied with a forefinger at 0.03 to 0.05 mL to discrete sites normally covered by a mask: namely, 1. Alar crease. 2. External nares. 3. Lateral cheek. 4. Nasolabial folds. 5. Philtrum. 6. Vermilion, and 7. Chin, as shown in FIG. 9. All sites gave coolness and cold sensations at various intensities, but, surprisingly and unexpectedly, only gel application on the external nares gave robust and effective relief of face mask discomfort. For coolness and cold, the rank order of the sites was alar crease>nares≡philtrum>vermilion≡nasolabial folds>chin>>lateral cheek. Surprisingly, for mask discomfort, relief was site-specific. For example, the application of the gel to the nasolabial folds or lips did not relieve discomfort, whereas application to the skin of the external nares (nostrils) was instantly effective. Further discussion with the test subjects illuminated the mechanism of drug action.

The test subjects stated that if the nose felt cold, air movement with each breath also felt fresh and cold, and the resistance to breathing disappeared. If the skin felt cold on the nasolabial folds or the chin, this refreshed breathing was not present, and the discomfort of the mask remained. This result also provides a hypothesis for why masks are uncomfortable. The constant breathing of static warm air causes discomfort. Refreshed breathing is a dynamic event governed by air coolness. The air has to move. With a mask, the subject feels suffocated. With cooling, there is a relief of discomfort. Earlier studies showed that dynamic and not static neuronal discharges into the brain account for the sensation of cooling in humans and that dynamic discharge is governed by the rate of temperature change. This refreshing cooling is also an event that requires the discharge of cooling TRPM8 nerve fibers. A cooling agonist applied to the nostrils enhances this TRPM8 neuronal event.

To further investigate this discovery, a method for selective drug delivery to the skin of the nares was improvised. The hollow of the volar palm forms a receptacle that holds about 0.5 to 1 mL of liquid. An ideal method to deliver a drug to the external nares is to place a solution into the hollow and immerse the nose tip into the hollow for ~5 sec. This technique allows comparisons of molecular potency and duration. For example, to construct dose-response data, a TRPM8 agonist solution was stored at a fixed volume in a disposable reservoir unit (3 mL polyethylene bottle) at 0.25 to 4 mg/mL solution in saline. Next, 0.8 mL aliquot is dispensed onto the hollow of the palm. Then the anterior nose is immersed into the hollow at a ~45° angle for 5 sec, as shown in FIG. 10. The tip of the nose fits snugly into the palmar cavity and precisely delivers the test solution to the skin of the nostrils. Inhalation of the solution into the nasal cavity itself is optional but not necessary. Alternatively, use a gel in the hollow of the palm or directly on the flares.

Surprisingly, this method of contacting the skin of the nares with a TRPM8 agonist yielded reliable dose-response data, as shown in FIG. 11. In practice, a single local application of DIPA-1-7 at 2 mg/mL in saline is sufficient to overcome mask discomfort for at least 4 hr and can be repeated with equal effect for another 4-hr period. By comparison, localized wiping of the DIPA-1-7 to other facial areas, such as the upper lip, philtrum, lips, and chin, were less effective for reducing mask discomfort.

Further improvement for the analysis of precise site of drug action on the nares was achieved by formulating the cooling agonist into a gel for drug delivery. This gel was then applied to different parts of the nares, as shown in FIG. 13. The surfaces of the nares can be divided into seven topographical subunits, as shown: 1. infralobular triangle, 2. central columella, 3. columella base, 4. nasal sill, 5. alar wall, 6. lateral wall, and 7. soft-tissue triangle. The soft-tissue triangle is a landmark for the use of a plastic or cotton tipped applicator containing the cooling gel. The "soft triangle pocket" target is marked with a cross on the illustration. Optimal cooling is achieved when the gel is delivered onto this pocket.

The mechanism of action of DIPA-1-9 for the relief of mask discomfort can be described in non-technical language. The skin of the nose around the nostrils and in the nasal vestibule, has sensors for temperature in the cool range of less than 25° C. These "thermistors" or TRPM8 nerve endings are activated by cold, such as on a cold day or on the ski slope, wherein the subject has a "runny nose." The sensors also convey the pleasure of breathing cool air by the seaside or on a breezy day. The sensors shut off behind a face mask when airflow is impeded or occluded, and heat accumulates above 22 to 25°+C (FIG. 3). This shut-off was elegantly studied and shown in Zakharian et al., (2010. "Gating of Transient Receptor Potential Melastatin 8 (TRPM8) Channels Activated by Cold and Chemical Agonists in Planar Lipid Bilayers." J. Neurosci. 30 (37): 12526-34). There is no air movement behind the mask. In the natural state the sensors respond best to the rate of temperature change, not static temperature. Applying a TRPM8 receptor agonist, such as DIPA-1-7 to the skin of the nostrils, restores and enhances the thermosensitivity to coolness. The air-conditioning system re-adjusts, and the subject feels better with a sense of cooler airflow when breathing. Now, the subject pays less attention to the annoyance of the facial covering.

Current thinking on face mask discomfort is focused on hear accumulation. But inhaled air is rapidly warmed to body temperature and humidified in the nasal cavity. The skin temperature and the temperature of the exhaled breath remains constant at ~34.5° C. Wearing an N95 respirator increases oral temperatures by only 0.27° C., but aural (or core) temperatures remain unchanged (Yip et al., 2005. "The Effect of Wearing a Face Mask on Body Temperature." Hong Kong J. Emergency Med. 12 (1): 23-27). When the use of the mask is prolonged, there is heat accumulation behind the mask, and the upper lip skin temperature increases by 1 to 2° C. (Roberge et al, vide supra). Heat and pain fibers such as TRPV1 do not activate until ambient temperatures reach 43.6° C. Temperature increments of this magnitude per se cannot explain face mask discomfort because the changes are too small!

The research here pinpoints the skin of the nostrils and the nasal vestibule as the critical sensory site for causing mask discomfort. Heat accumulation per se is not sufficient to cause discomfort. It is the absence of air movement and decreased TRPM8 neuronal discharge at the nostrils that trigger discomfort and psychological distress: an absence of "cool air dynamics". In a hot air environment, evaporative heat loss is the only trigger for TRPM8 activation, but evaporation requires air movement and <100% humidity, which are both diminished with a mask. The sensations of suffocation and dyspnea may also originate from TRPM8 sensors' dysfunction at this site. To summarize the concept proposed:

Face Mask discomfort=reduced air movement around the nostrils+no TRPM8 cooling signals. A rise in skin temperature of 1 to 2° C. is not essential because skin temperatures are already above 34° C. The discomfort is caused by an absence of "cool air dynamics."

Relief of Face Mask Discomfort=supplying a potent agonist of TRPM8 signals to simulate cool air dynamics to receptors on nostrils and nasal vestibule.

An essential part of this discovery is the recognition that the nostrils' skin is highly sensitive to thermal stimuli and influences airflow comfort and discomfort. The second part of the invention identifies selective TRPM8 agonist molecules that can be precisely delivered to the nostril site to relieve mask discomfort. A third part of the discovery is the development of a gel formulation for swift delivery to target receptors via the soft triangle pocket. The size of the gel drop for application is ≤0.1 mL and composed of ≥98%. The prior art does not pinpoint this anatomical site for causation of discomfort or a method of selective topical delivery of a cooling agent to the nares skin for the treatment of mask discomfort.

Thus, in one aspect of the invention a method for the treatment of sensory discomfort in a subject who will be wearing a facial mask covering for more than one hour comprises topically applying a liquid or semi-liquid composition to the skin of the subject's nares, the composition having a therapeutically effective amount of a compound with Formula 1 therein Formula 1 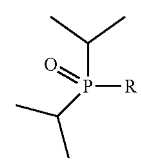 wherein R is n-pentyl, n-hexyl, n-heptyl, n-octyl, or n-nonyl and wherein the composition is carried by a delivery agent, the agent being adapted to deliver the Formula 1 compound when topically applied with the Formula 1 compound thereby penetrating the skin of the nares skin and being therapeutically effective to at least reduce, and preferably eliminate, the sensory discomfort while the subject continues to wear the mask.

In another aspect of the present invention a method for the treatment of sensory discomfort in a subject caused by the subject's wearing a facial mask covering for more than one hour comprises providing a liquid or semi-liquid composition carried by a delivery agent, the composition having a therapeutically effective amount of a compound with Formula 1 therein when the composition is topically applied so as to penetrate the skin of the nares Formula 1 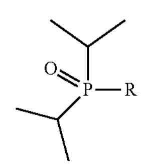 wherein R is n-pentyl, n-hexyl, n-heptyl, n-octyl, or n-nonyl; and, instructing the subject to topically apply a therapeutic dose of the composition to the skin of the subject's nares, the therapeutical effect such that the subject can continue to wear the facial mask with reduced or eliminated sensory discomfort.

BRIEF DESCRIPTION OF THE SEVERAL VIEWS OF THE DRAWINGS

FIG. 13. is an illustration of the method for delivering a cooling gel to the surfaces of the nostrils and nasal vestibule. The surfaces of the nares can be divided into seven topographical subunits, as shown: 1. infralobular triangle, 2. central columella, 3. columella base, 4. nasal sill, 5. alar wall, 6. lateral wall, and 7. soft-tissue triangle. The soft-tissue triangle is a landmark for the use of a plastic or cotton tipped applicator containing the cooling gel. The "soft triangle pocket" target is marked with a dashed circle on the illustration. The gel drop applied is ≤0.1 mL and composed of ≥98% water.

DETAILED DESCRIPTION OF THE INVENTION

Dr. Wu Lien-Teh first established the use of modern face masks (Lee et al., 2014. "Dr. Wu Lien-Teh: Modernising Post-1911 China's Public Health Service." Singapore Medical J. 55 (2): 99-102). He was a physician from Malaya of Chinese descent who went to Cambridge, UK. In 1910-1911 he was asked to control an airborne bubonic plague epidemic in Manchuria. He designed a cotton pad wrapped in gauze, which helped reduce transmission. The value of these masks was recognized, publicized, and used in the Spanish flu epidemic of 1918. Concurrently, "surgical masks" became standard for surgeons in the operating theater. Improvements in mask design and mass manufacture accelerated after the SARS-CoV episode in 2003. The use of masks in Japan became commonplace in 2009 because of fear of H1N1 influenza and the proximity of people in mass transit. Now in 2020, because of the COVID pandemic, wearing masks is as common as eating rice, potatoes, hamburgers, or drinking alcohol.

In the current CoV pandemic, HCW such as doctors and nurses use an N95-FFR (filtering facepiece respirator), which is fitted to the wearer and reduces risks of infection. The general public mainly wears a face mask (FM), which is loose-fitting and protects less against the virus. The facial covering in both types of masks leads to discomfort after continued use, especially when the environment is hot. The exact causes of mask discomfort are not known. The discovery here suggests that a cooling agent applied to the skin of the nostrils effectively prevents and reduces mask discomfort. In the present discovery, a gel containing a designed TRPM8 agonist is applied to the skin of the nose and the vestibule to reduce mask discomfort. The gel content facilitates coolness and airflow signals and is not intended for access to the nasal mucosa.

Sensory Discomfort of Masks and Respirators

A facial covering is an artificial and unnatural event that is a barrier for air and heat exchange. Wearing a mask in hot weather or a stressful environment is unpleasant (Johnson, A. 2016. "Respirator Masks Protect Health but Impact Performance: A Review." J. Biol. Engineering 10 (1): 1-12). The mask covers the skin over the triangular surface area delineated by the nose's bridge, the nasolabial folds (smile lines), and the lower lip and parts of the chin. Heat and water vapor accumulates behind the mask and acts on thermosensors on the skin and nasal cavity. Airflow is confined and static. The enclosed surfaces of the skin of the nostrils, the alar crease, and the vermilion are especially sensitive to heat. Receptors that sense air temperature and humidity are also densely present in the anterior nasal vestibule and, internally in the nasal cavity.

Figure 12:
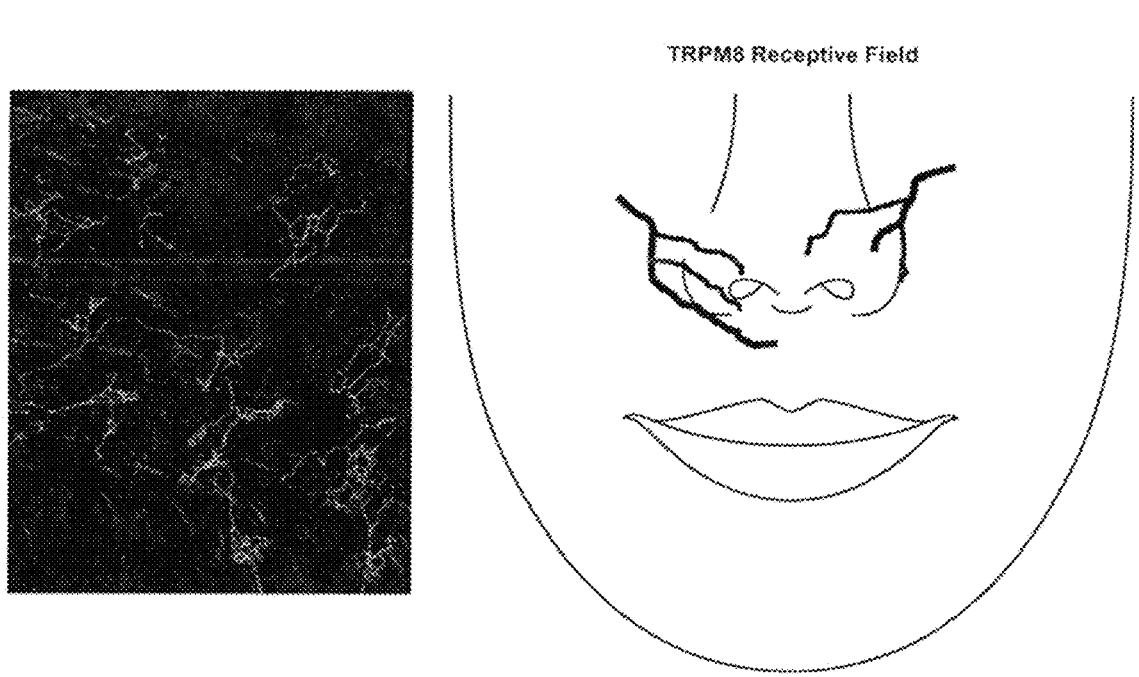
FIG. 12. is an illustration of the neuronal receptive field for the delivery of the preferred embodiments. The nostrils, including the nasal vestibule, are keratinized skin surfaces innervated by the infraorbital nerve (right side of nose) and the external branch of the anterior ethmoidal nerve (left side of nose). These sensory nerves contain TRPM8 nerve fibers which may be visualized as green fluorescent fibers in transgenic mice (e.g., see Wei, E. T. 2020. Medical Hypotheses 142. 109747. https://doi.org/10.1016/j.mehy.2020.109747].).

The sensory signals from the skin and nasal structures are transmitted by the facial nerve and the trigeminal nerve to the brain and integrated into temperature perception and regulation. The first step to understanding the mechanisms of face mask discomfort is identifying and defining the neuronal receptive fields and appendages of the cranial nerves covered by the face mask. The buccinator innervates the ~10-15 keratinized layers of squamous epithelia on the cheek. The mental nerve innervates the chin. The infraorbital nerve innervates the alar crease, nasolabial folds, nostril skin, upper lip, philtrum and vermilion. The vermilion does not have a stratum corneum and is only 4 to 5 cell layers thick. Other perioral surfaces are keratinized epithelia. The external branch of the anterior ethmoidal nerve innervates the nasal skin, nostrils, and the nasal vestibule. As shown in the specifications, the application of a cool TRPM8 agonist is most effective when applied to the receptive fields of the infraorbital and the external anterior ethmoidal nerve (FIG. 12). This application method is with a preferred embodiment formulated in a gel and put onto the "soft triangle pocket" of the nose using a tipped-applicator.

Thermal comfort is a balance of afferent inputs from the sensory nerves of the face. The dynamic sensitivity of the facial area and nasal cavity to heat is higher than the sensitivity of the torso's skin. The signals are centrally integrated for perception. Cooling of the face is two to five times more effective at suppressing sweating and thermal discomfort than cooling an equivalent skin area elsewhere on the body (Cotter and Taylor, vide supra). The greater sensitivity of the facial skin to coolness is self-evident when one uses an air-conditioner. The cool air is more effective when blown over the face than over the body.

Inhaled air is rapidly warmed to body temperature and humidified in the nasal cavity. The skin temperature and the temperature of the exhaled breath remains constant at ~34.5° C. Wearing a face mask or an N95 respirator increases oral temperatures by only 0.11° C. and 0.27° C., respectively, but aural temperatures remain unchanged (Yip et al., vide supra). When the use of the mask is prolonged, there is heat accumulation behind the mask, and the upper lip skin temperature increases by 1 to 2° C. (Roberge et al., vide supra). Heat and pain fibers such as TRPV1 do not activate until 43.6° C. Temperature increments of less 0.5° C. per se cannot explain face mask discomfort because the changes are too small! Nevertheless, a higher ambient temperature, together with wearing an impermeable surgical gown, aggravates mask discomfort.

The subjects complain of increased resistance to airflow when breathing, heat behind the mask, difficulty in communication to others, and skin irritation. There is also a loss of concentration, perceptual disorientation, and increased heart rate. These signs and symptoms are common in subjects exposed to environmental heat stress, but in mask users, the heat stress is only on the face and not the rest of the body.

Respirators and masks protect if HCW adheres to use. In an 8-hr work shift, 59% of the workforce discontinued wear, citing communication difficulties (visual, auditory, or vocal), heat, pressure or pain, and dizziness or difficulty concentrating. Median tolerance times ranged from 4.1 to 7.7 hours. Wearers of disposable models often complained of facial heat and pressure, while users of reusable models often reported communication problems. A cup-shaped N95-FFR with an exhalation valve had a better median tolerance time (7.7 hours) than a similar model without a valve (5.8 hours). In a survey of users, only 24% reported that their N95-FFR respirator was comfortable most of the time or always, but only 6% said that they would tolerate wearing it for an 8-hr shift. The problems identified were discomfort, difficult breathing, heat, and low tolerability for an extended time.

In a controlled environment study of 10 nurses, the compliance rate to two-12 hr shifts wearing an N95 respirator was 78%. There were, however, subjective symptoms of perceived shortness of breath, complaints of headache, lightheadedness, hindered communication, and feelings of nausea. MacIntyre et al. (vide supra) showed that facial coverings protect HCW against chronic respiratory illnesses. Masks also protected nurses during a SARS outbreak in Toronto. Thus, increased adherence or compliance to wearing a mask may be a life-saving event (see Loeb et al. vide supra).

Cryosimulator Unit

A cryosimulator unit is a unit for the delivery of a TRPM8 agonist to its defined receptive field [Wei, E. T. 2020. "Improving Brain Power by Applying a Cool TRPM8 Receptor Agonist to the Eyelid Margin." Medical Hypotheses 142 (April): 109747. https://doi.org/10.1016/j.mehy.2020.109747]. The delivery unit may, for example, be a topical gel, a unit dispenser with a fixed volume solution, a rinse, a swab, or a wipe.

A water-soluble TRPM8 agonist such as DIPA-1-7, applied topically, instantly cools the nasal area, gives a sense of free-breathing, and relieves heat discomfort. The best cryosimulator unit for mask discomfort is a topical gel or a solution applied via the hollow of the palm to the nares. The cryosimulator unit here acts topically like a mini air conditioner for the nasal skin. In addition to the skin, another source of dynamic thermal information comes from the nerve endings of the epithelia inside the nasal vestibule. The respiratory epithelium of the nasal cavity is not the primary target. Nasal sprays are not preferred because the hospital environment should avoid creating infectious airborne particles. The skin over the nares is ideal for drug delivery because air move over these thermosensors. Other facial skin, such as those innervated by the facial, trigeminal, or infraorbital nerves, may contribute information on the status of coolness/cold in the environment, but the response dynamics are less sensitive.

The receptor coding for and transducing cool/cold signals follows a discrete "cable" line coded by the receptor called TRPM8 [Knowlton et al. 2013. A sensory-labeled line for cold: TRPM8-expressing sensory neurons define the cellular basis for cold, cold pain, and cooling-mediated analgesia. J. Neurosci. 33, 2837-48]. The sensory neurons for TRPM8 do not overlap with the neurons coded for intense heat, such as the TRPV1 receptor. The mechanism of interactions is via indirect gating of neuronal signals. TRPM8 signals suppress heat signals centrally in the brain, not in the periphery.

The detailed molecular characteristics and physiology of TRPM8 are known. Amino acid residues important for binding and function are identified, and the TRPM8 structure has been clarified by cryo-electron microscopy to a resolution of ~4 Ångstroms [Pertusa et al., 2018. Critical role of the pore domain in the cold response of TRPM8 channels identified by ortholog functional comparison. J. Biol. Chem. (2018) 293: 12454-1247; Yin, Y. et al., 2019. Structural basis of cooling agent and lipid sensing by the cold-activated TRPM8 channel. Science. 2019 Mar. 1; 363]. When the temperature is ≤25° C., TRPM8 pores open up, and entry of cations across nerve endings triggers action potentials to the brain, activating cool/cold signals from the specific receptive field. Chemical cooling agents such as menthol or icilin facilitate the opening of TRPM8 pore. TRPM8 nerve endings discretely aggregate in the body [Dhaka, et al., 2008. Visualizing Cold Spots: TRPM8-Expressing Sensory Neurons and Their Projections. J. Neurosci. 28, 566-575]. In rodents, there is a high density of innervation in the whisker pad and the skin. The TRPM8 nerve fibers can be visualized as green immunofluorescence in transgenic mice.

Mechanism of Action, Receptor Target, Selection of Active Ingredient

Relief of mask discomfort requires the selection of the best receptor agonist. The target location must be defined, and the formulation and concentration prepared in a delivery system to give sufficient duration of action. The time for delivery is optimized to when cooling is needed.

An agonist is a chemical activator of biological events [Reuse, J. J., 1948. Comparison of various histamines antagonists, Brit. J. Pharmacol. 3: 174-180]. A TRPM8 agonist acts on a binding site of TRPM8 to facilitate the opening of the receptor pore. After entry of cations into the pore, action potentials are generated and transmitted into the central nervous system. The threshold for feeling cool goes down. For the selection of an active ingredient, there are four major classes of TRPM8 agonists: a) the monoterpenes as represented by 1-menthol, b) icilin, c) p-menthane carboxamides and related cyclohexane derivatives, such as WS-5 and WS-12, and d) 1-dialkylphosphorylalkanes. Menthol does not work well on the nasal skin. It must be dissolved in an organic solvent such as alcohol, it irritates the eye surface, and also causes rhinorrhea. Icilin is practically insoluble in any solvent, so delivery is problematic. The p-menthane carboxamides and esters need a solvent system before delivery, but gels or creams are possible. By experiment, ideal agents identified here are water-soluble 1-dialkylphosphorylalkanes called DIPA compounds. Preferred embodiments are DIPA-1-7 [Cryosim-1,1-diisopropylphosphorylheptane, CAS Registry No. 1487170-15-9], DIPA-1-8 [Cryosim-2, 1-diisopropylphosphoryloctane, CAS Registry No. 2959-63-9], and DIPA-1-9 [Cryosim-3, 1-diisopropylphosphorylnonane, CAS Registry No. 1507344-37-7]. These compounds are active at concentrations of 0.5 to 2 mg/mL dissolved in water or saline and have the desired cooling actions. Yang et al. [Wei is co-author, 2017. A novel TRPM8 agonist relieves dry eye discomfort BMC Ophthalmology (2017) 17:101, 1-15. doi:10.1186/s12886-017-0495-2] described the pharmacology of DIPA-1-9. This reference is incorporated into this application by reference.

DIPA-1-7 [Cryosim-1,1-diisopropylphosphorylheptane, CAS Registry No. 1487170-15-9] is effective for mask discomfort, especially when formulated into a gel.

Delivery System

An essential part of hypothesis testing is to use a gel, solution, or wipe to deliver a cool TRPM8 agonist to the receptors on the skin of the nares and the epithelia of the nasal vestibule. A familiar form of drug delivery is to use a gel applied with either a finger to the nostril or an applicator, such as a cotton swab. Alternatively, a formulation for the palm hollow, with instructions to rub a subject's nose tip into the hollow, works well. These methods are preferable to drops, sprays, or wipes because the delivery is exactly over the nares, but the methods require explicit instructions to the user. The topical route avoids the likelihood of systemic side effects. For a gel, an adequate volume is ~0.05 to 0.2 mL and for a liquid, an aliquot of ~0.6 to 1.0 mL. For a solution, instruct subject to incline face at ~45° and place nose tip into palm hollow for ~5 sec, as show in FIG. 10. For a rinse, an adequate volume is 5 to 20 mL and the concentration of the DIPA compound is 0.05 to 0.25 mg/mL. The method for applying a gel onto the "soft triangle pocket" is shown in FIG. 13.

For each molecule, activity is a sum of penetration, distribution, localization, and intrinsic actions at the receptor. The discovery of the best compounds for the skin of the nares is by iterative experiment. The preferred embodiments for mask discomfort are 1-[Dialkyl-phosphinoyl]-alkanes [(O=)PR$_1$R$_2$R$_3$] wherein each of R$_1$, R$_2$, is isopropyl and R3 is a linear alkyl group of 5 to 9 carbons, and wherein the embodiments have 15 or 16 carbons. Such compounds are DIPA-1-6, DIPA-1-7 and DIPA-1-8. The "mixed 3,4-X analogs" and the disec-butylphosphoryl analogs may also be considered, but have not been fully explored.

The ideal agent must act locally, and the intensity of the sensation should not cause "icy cold," rhinorrhea, icy pain on the dome of the nostril, coldness in the chest, or systemic chills. One preferred embodiment is DIPA-1-7 because it is water-soluble and has rapid onset of activity, and because the gel formulation does not over-activate the cold receptors in the nasal skin. Ideally, the preparation should be easy to formulate, apply, have a rapid onset of action, for example, within 1 to 3 min after application, absence of irritation at the site of application, absence of systemic effects, and sufficient duration of action to prevent mask discomfort for 3 to 4 hr. Proof of efficacy to relieve mask discomfort may requires a randomized, double-blind, and placebo-controlled trial with quantitative parameters of patient outcomes. Such parameters may be a visual analog of mask comfort and time of mask use as an indicator of adherence.

Hypothesis on Mechanism of Action

Studies by Hutchinson et al. (vide supra) show the inverse relationship between the discharge of hot and cold units when temperature changes on the whisker pad of the anesthetized rats. He recorded units from the trigeminal inputs into the medulla. As shown by Zakharian et al., 2010 (vide supra), TRPM8 firing shuts off when temperatures rise above 22° C. From these results, the hypothesis proposed here is that the "shut-off" of TRPM8 nerve inputs from the face triggers mask discomfort. It is not an excess of warmth signals, but the absence of fresh cool signals that trigger mask discomfort. The shut-off from the receptive fields of tissues surrounding the "soft-triangle pocket," namely, the central columella (FIG. 12), lateral wall, soft-tissue-triangle, and adjacent nasal vestibular wall has the most impact on discomfort. A cool TRPM8 agonist counteracts this "shut-off" and replenishes the TRPM8 signals. The surprising inference and conclusion are that it is an absence of cooling at a specific locus and not a general excess of warmth that causes mask discomfort.

Descriptors and Terminology

Cryosimulator unit (CSU) A cryosimulator unit is a unit for the delivery of a TRPM8 agonist to its defined receptive field. The delivery unit may be in the form of a bolus of water, a wipe, a dropper with a reservoir, a unit dispenser, a rinse, a swab, or a topical gel. In this discovery, the preferred CSU is a gel or a 1 mL volume of liquid (e.g., 1 mL of DIPA-1-9 in saline) placed in the cup of the volar palm, and applied to the nostril of the mask wearer with instructions to contact the liquid content.

Intrinsic® IB Spot Serum from Donghwa Pharmaceutical Co., Ltd., Seoul, Republic of Korea, which contains 1.5% wt/vol of DIPA-1-7 as its main component, was used as the "active" test gel to identify the facial sites for mask discomfort. The placebo gel consisted of gel, but without the DIPA-1-7. Neither the patients nor the clinician investigator was made aware of the test substance. The test subjects applied a small amount with the fingertip as needed, to the topical area.

DIPA compounds DIPA is the abbreviation for 1-[Diisopropyl-phosphinoyl]-alkane or 1-diisopropylphosphorylalkane. A number describes the third alkyl group in the molecule: hence, 4, 5, 6, 7, 8, 9, and 10 correspond to the butyl, pentyl, hexyl, heptyl, octyl, nonyl, and decyl side chain, respectively. These alkanes are linear or "normal [n]" in configuration, with the phosphinoyl group attached to the primary, or "1-" position, of the carbon chain in the third sidechain. These compounds are also known as trialkylphosphine oxides or as 1-dialkylphosphorylalkanes.

Discomfort of Wearing Masks There are three main types of complaints in mask discomfort. One is an increased effort in breathing, i.e., there is a sense of resistance to airflow caused by fabric in the mask. A second sensation is that of accumulated heat and humidity behind the mask with sensations of suffocation and impaired ventilation. The third type of symptom is disturbed perception, a lack of concentration, and an inability to perform routine tasks efficiently. Somatic signs and symptoms of sympathetic nervous system activation, e.g., increase in heart rate and blood pressure, may also be present.

Figure 3:
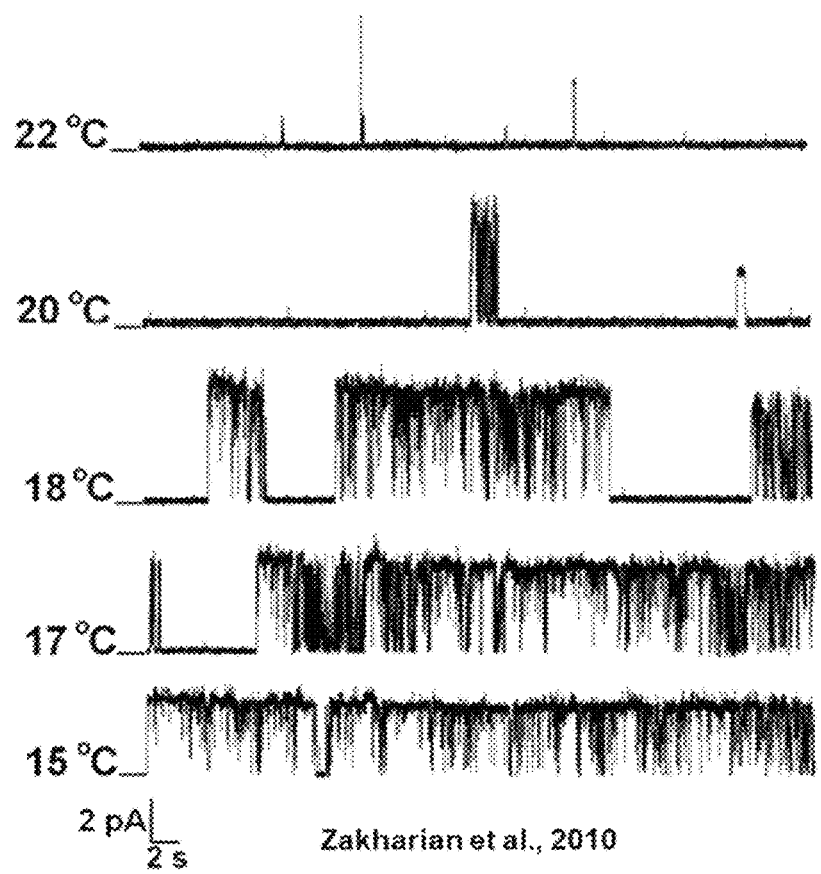
FIG. 3. is an illustration of electric discharge in a lipid bilayer containing a TRPM8 receptor protein (Zakharian et al., 2010). The discharge frequency measured by patch-clamp techniques is influenced by the ambient temperature of the receptor. When temperature goes above 22° C. discharge frequency is decreased and maximally increased when the temperature is lowered to 15° C.

Dynamic Cooling. Small myelinated (As) and unmyelinated fibers (C fibers) increase afferent firing rate when skin temperature decreases, for example, between 35° C. and 15° C. The neuronal signals that detect heat abstraction transmit to the central nervous system for perception of coolness and cold. Raising temperature from 35° C. and 40° C. increases firing rates in C fibers to signal warmth [Hutchinson et al. Quantitative analysis of orofacial thermoreceptive neurons in the superficial medullary dorsal horn of the rat. J. Neurophysiol. 77, 3252-66, 1997]. The receptive mechanisms and "cable lines" for cool/cold are separate and distinct from warm fibers, but reciprocally inhibit each other in the brain and perhaps also in the periphery. The sensory receptors are modality-specific and do not respond to mechanical stimulation. At the molecular level, the target binding sites for cooling agents are on TRP ion channel receptors that depolarize in response to a drop in temperature. Heat abstraction decreases the threshold for discharge of the receptor, and the facilitated depolarization initiates the axonal responses that create the neuronal signal (FIG. 3).

The central response of these neurons has been recorded and studied from rat superficial medullar dorsal horn that responds to innocuous thermal stimulation of the rat's face and tongue [Hutchinson et al., vide supra 1997]. Step changes of $-\Delta 5°$ C. stimulated cells with both static firing rates and cells that had mainly dynamic properties [Davies et al. Sensory processing in a thermal afferent pathway. J. Neurophysiol. 53: 429-434, 1985]. Similar studies in cats and humans showed that step decreases in temperatures (dynamic changes), as low as $\Delta 0.5°$ C./second, were readily detectable by neurons and by psychophysical measurements [Davies et al. Facial sensitivity to rates of temperature change: neurophysiological and psychophysical evidence from cats and humans. J. Physiol. 344: 161-175, 1983].

A study of the spike patterns of neuronal discharge (impulses/second) showed that dynamic, and not static firing responses to a change in temperature were the most potent stimuli for generating coolness/cold sensations. That is, the brain "sees" $-\Delta°$ C./t and not absolute ° C. Thus, a cooling agent that simulates $-\Delta°$ C./t on nerve discharge evokes "dynamic cooling."

Face Masks (FM) Face masks, also called surgical or medical masks, are loose-fitting coverings of the nose and mouth, designed to protect the patient from secretions from the nose or mouth of the physician, nurse, or other healthcare professional. Face masks are also used by the wearer to reduce exposure to respiratory hazards.

N-95-Face Filtration Respirators (N-95-FFR or KN95-FFR) Protective respirators work by filtering the air inspired by the wearer. N95-FFR are certified and cleared as medical devices by government agencies such the Food and Drug Administration (FDA). Effective respirators must fit tightly to the face.

Facial mask discomfort and heat stress Thermal comfort is a technical term used by air-conditioning engineers to define "a state of mind in humans that expresses satisfaction with the surrounding environment." Maintaining thermal comfort for occupants of buildings or other enclosures is one of the essential goals of architects and design engineers. For most people, the room temperature for thermal comfort is 20 to 25° C. Careful studies have documented that work performance and productivity drop by 2% for every increment of +1° C. above 25° C. up to 33° C. At office temperatures of 28-30° C. (82-86° F.), there is sweating and complaints of headache, drowsiness, and dullness, difficulty in concentrating, and physical discomfort and loss of work performance [Tanabe et al., 2007. Indoor Air Quality and Productivity. REHVA Journal 44(2) 26-31]. An ambient temperature above 25° C. is thus a form of heat stress. Symptoms and signs of general heat discomfort are similar to mask discomfort.

Gel for Delivery to Nasal Skin. In the US Pharmacopeia "gels" are defined as a semi-solid system consisting of molecules interpenetrated by a liquid. Single-phase gels consist of molecules uniformly distributed throughout a liquid with no apparent boundary between the dispersed molecule and liquid. For the 1-dialkylphosphoryalkanes, the active ingredient is water-soluble at active concentrations (0.01 to 5%); hence it formulates as an aqueous single-phase gel. In pharmaceutical formulations, the advantages of a single-phase system are lower costs and simplicity. For example, the DIPA preferred embodiments described here are miscible with water at 30+ mg/mL.

The Lubrizol® Company created Carbopol® polymer products over 50 years ago. These polymers are used in pharmaceuticals as rheology modifiers, suspension stabilizers, and bioavailability enhancers. The polymers, popular as excipients, are high molecular weight, crosslinked polyacrylic acid polymers. The specific Carbopol polymer used in this discovery (980 NF) is a Carbopol homopolymer comprised of acrylic acid crosslinked with allyl sucrose or allyl pentaerythritol. Carbopol 980NF was made using cyclohexane and ethyl acetate as solvents and thus free of benzene. The viscosity of a 0.5% wt/vol solution of 980NF in water at pH 7.5 is 40,000 to 60,000 centiPoise (cP). For comparison, 1 is the cP of water, 10,000 for honey, 50,000 for ketchup, and 250,000 for peanut butter. A preferred embodiment gel was created by mixing 360 mg of 1-diisopropylphosphorylheptane (DIPA-1-7) with 60 mL of distilled water, plus 300 mg Carbopol 980 NF and centrifuging the mixture at 3000 rpm for 5 min in a FlackTek Mixer. The gel is clear, translucent, and suitable for topical applications. The high-speed FlackTek centrifuge is a technical aid for mixing. The concentration of DIPA-1-7 is 6 mg/mL.

Gel application is either with a cotton [Puritan (Gullford, Me., USA) 803 PCL] or plastic tipped applicator. For the cotton applicator the load was 64±3 mg (n=25 trials), and the off-load 24±2.6 mg. For the plastic applicator, the load was 76±4 and the off-load was 66±4. The off-load of 87% with the plastic tip was better than the 36% with the cotton tip. The application can be repeated per nostril. The DIPA-1-7 gel is effective in reducing face mask discomfort for ~4 hr. The delivered volume per application was ≤0.1 mL and the gel drop contained ≥98% water (0.5% Carbopol and ≤1.2% of preferred embodiment).

Healthcare Workers (HCW) or Healthcare Personnel broadly encompass all workers in direct patient care and support services who are employed by private and public healthcare offices and facilities as well as those working in home healthcare and emergency medical services, including those who are self-employed.

Hollow of the Palm Assay. The cavity in the center of the volar palm formed by the thenar and hypothenar muscle contraction conveniently forms a receptacle for the nares (FIG. 10) Palmists call it "Plain of Mars," and the centerline "Fate Line." To assay, load hollow with ~0.05 to 1 mL and immerse nares into hollow for ~5 sec.

Nares. The nares (singular, naris), or nostrils, are the pair of openings immediately below the tip of the nose and are the entrances to the respiratory tract. The nasal passages serve as a conduit for inspired and expired air. When these passages have increased resistance to flow, are congested, or obstructed, subjects perceive it as uncomfortable. The skin above the nares are sensitive to heat and cold. The nares can be divided into seven topographical subunits, as shown in FIG. 13.: 1. infralobular triangle, 2. central columella, 3. columella base, 4. nasal sill, 5. alar wall, 6. lateral wall, and 7. soft-tissue (ST) triangle.

Nasal patency—is the subjective sensation of openness and smooth airflow in the nasal passages when breathing. Loss of patency may be reported as "nasal stuffiness" or "nasal blockage" and causes discomfort, and the subject may use mouth breathing, which is undesirable because it desiccates the airway surfaces. Nasal congestion implies excess fluids in the nasal passages. The term "nasal obstruction" means there is a structural hindrance to airflow. Rhinitis, the inflammation of the membranes in the nasal cavity, is most often associated with nasal congestion and nasal obstruction. In the "empty nose syndrome," there are severe breathing discomforts, including loss of the sense of patency, but the symptoms can occur without rhinitis or physical evidence of change in airflow or gas exchange [Sozansky, J. Pathophysiology of empty nose syndrome. Laryngoscope 125, 70-74 (2015)]. For this drug discovery, the drug action is on the perception of free airflow and heat discomfort, an action on the skin and not on nasal patency which is more of a problem of nasal mucosa dysfunction.

The nasal afferents for detecting temperature are on branches of the trigeminal nerve. Receptors that mediate detection of coolness is the cation channel called TRPM8. Keh et al. [The menthol and cold sensation receptor TRPM8 in normal human nasal mucosa and rhinitis. Rhinology 49, 453-7 (2011)] have detected TRPM8 immunoreactivity in the human nasal mucosa, closely associated with nerve fibers and blood vessels.

Breathing cool air increases the sense of nasal patency. Inspired air temperature at the septum kept at 25 to 35° C., gives a greater sense of patency at the lower temperature [Willatt et al., vide supra]. However, it is also well-known that cold and frigid air evokes a "runny nose" or rhinorrhea, an event mediated by cholinergic nerves on serous glands of the nasal epithelium [Ostberg et al. Cold air induced rhinorrhea and high-dose ipratropium Arch. Otolaryngol. Head and Neck Surg. 113, 160-162 (1996)]. This condition has also been called a "skier's nose" and is quite common. Thermal receptors on the dome of the nose, at the anterior tip, may be especially sensitive to cold. Cooling of the nasal skin must avoid rhinorrhea, which is not desirable for a person wearing a mask. In a previous study, the preferred embodiments, DIPA-1-8 and DIPA-1-9, tested at a total dose of ~50 µg cooled the nasal cavity but not the nostril skin. These DIPA compounds require a higher dose on the facial skin for mask discomfort. DIPA-1-7, DIPA-1-8 and DIPA-1-9 were selected for the current indication of face mask discomfort because they were long-acting.

Breathing cool air, for example, at the seaside, enhances the sense of fresh airflow in the nose. In the laboratory, subjects report a greater sense of nasal patency with lower nasal septum temperatures [Willatt et al. The role of the temperature of the nasal lining in the sensation of nasal patency. Clin. Otolaryngol. Allied Sci. 21, 519-523 (1996)]. Peak mucosal heat loss in a critical region of the anterior nose is a key correlate of the sense of nasal patency [Zhao, K. et al. Regional peak mucosal cooling predicts the perception of nasal patency. Laryngoscope 124, 589-595 (2014)]. The benefit of cooling the skin of the nose for mask discomfort is a new concept.

Receptive field of a sensory neuron is the region in space in which a stimulus modifies the firing of the neuron. The receptive field is the spatial distribution of functional nerve endings of the neuron. For the epithelium, the nerve endings interdigitate with the cell layers at the epithelium's basal layer. A receptive field, as small as an $mm^2$, when activated by the appropriate stimulus, e.g., nociceptive or pruritic, can dominate the brain's and mind's attention. Witness what happens when a sharp pin or sting comes into contact with skin or when a dog is pre-occupied with a flea bite. The receptive field for the preferred embodiments are shown in FIG. 12.

Figure 1:
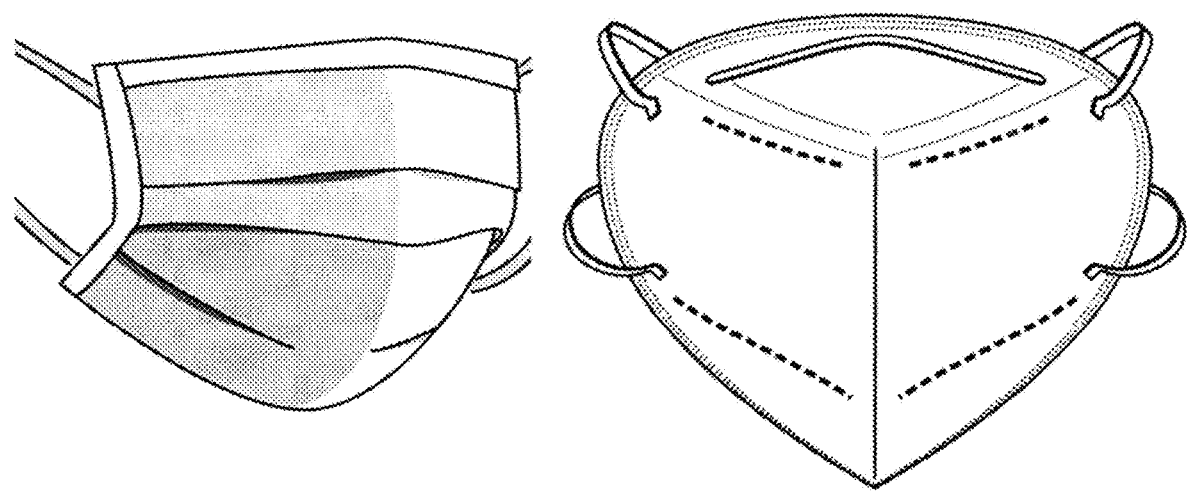
FIG. 1. is an illustration of filtering face masks that covers the nose and mouth of a wearer. Left: a facial mask, also called a surgical mask or medical mask. Right: an N95 facepiece filtering respirator.
Figure 2:
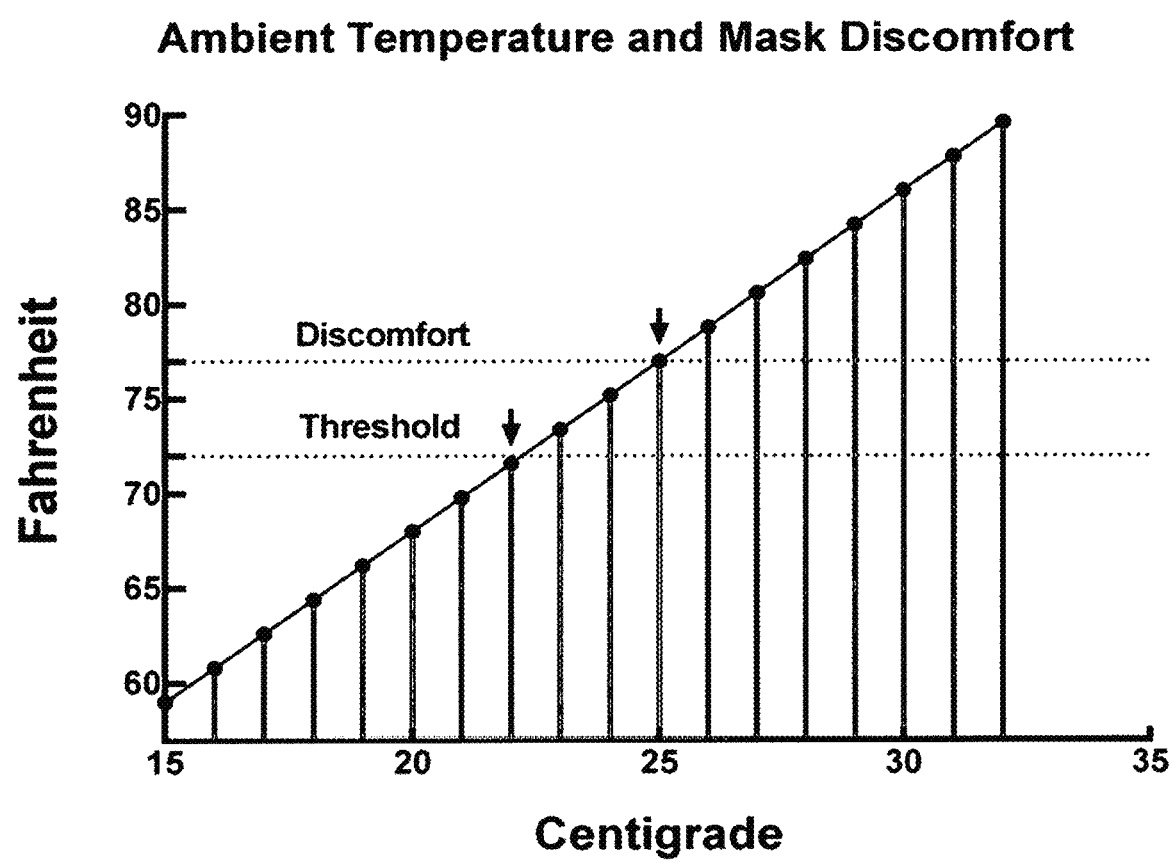
FIG. 2. is an illustration of the association of ambient temperature and mask discomfort. A tight-fitting N95 facepiece filtering respirator becomes uncomfortable after 1 hr of continuous use at room temperature and the discomfort is further aggravated when the ambient temperature rises above 25° C.
Figure 9:
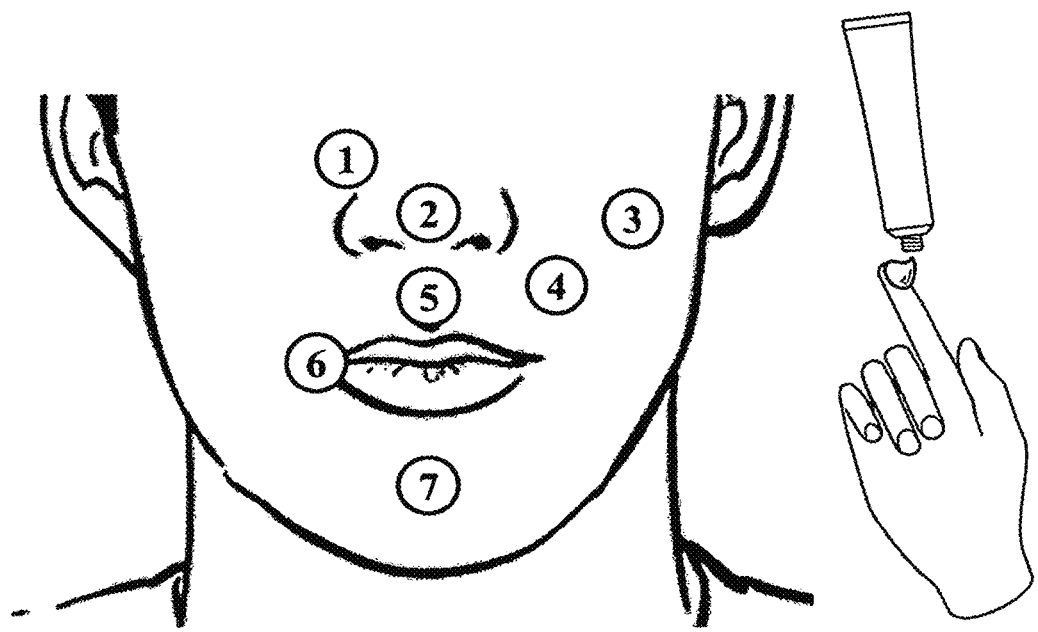
FIG. 9. is an illustration of the human face showing the test sites for applying a gel containing 1.5% (15 mg/mL) of DIPA-1-7. The sites are identified by the numbered circles: 1. Alar crease. 2. External nares. 3. Lateral cheek. 4. Nasolabial folds. 5. Philtrum. 6. Vermilion. 7. Chin. A 0.03 to 0.5 mL aliquot of a commercial gel containing 1.5% of DIPA1-7 (Intrinsic IB, Dong Wha Pharmaceuticals, Seoul, Republic of Korea) was applied with a forefinger to the designated site.

The cooling gel is delivered to the keratinized surfaces of the nose and not to the respiratory epithelium. The external features of the facial areas covered by a mask are shown in FIG. 9. The nares can be divided into seven topographical subunits, as shown in FIG. 13 1. infralobular triangle, 2. central columella, 3. columella base, 4. nasal sill, 5. alar wall, 6. lateral wall, and 7. soft-tissue (ST) triangle. The ST triangle is a landmark for the insertion and delivery of the gel to the receptor targets. Place thumb and forefinger on the top of the nose, and when you pinch, the tip of the digits are over the ST triangle. The name "soft" triangle comes from the lack of cartilage support in the triangle, as it is only skin and soft tissue. Keratin covers the nose and nasal vestibule's external layers, which are squamous epithelium with hair follicles (vibrissae), nerve endings, and sebaceous glands. The vestibular epithelium constitutes about 12% of the nasal surface area. Past the nasal valve area, the vestibular epithelium transits into a single layer of pseudostratified respiratory epithelium, which is the nasal mucosa.

FIG. 9. is an illustration of the human face showing the test sites for applying a gel containing 1.5% (15 mg/mL) of DIPA-1-7. The sites are identified by the numbered circles: 1. Alar crease. 2. External nares. 3. Lateral cheek. 4. Nasolabial folds. 5. Philtrum. 6. Vermilion. 7. Chin. A 0.03 to 0.5 mL aliquot of a commercial gel containing 1.5% of DIPA1-7 (Intrinsic IB, Dong Wha Pharmaceuticals, Seoul, Republic of Korea) was applied with a forefinger to the designated site.

FIG. 13. is an illustration of the method for delivering a cooling gel to the surfaces of the nostrils and nasal vestibule. The surfaces of the nares can be divided into seven topographical subunits, as shown: 1. infralobular triangle, 2. central columella, 3. columella base, 4. nasal sill, 5. alar wall, 6. lateral wall, and 7. soft-tissue triangle. The soft-tissue triangle is a landmark for the use of a plastic or cotton tipped applicator containing the cooling gel. The "soft triangle pocket" target is marked with a dashed circle on the illustration. The gel drop applied is ≤0.1 mL and composed of ≥98% water.

The vestibular epithelium (VE) and nasal mucosa (NM) contain sensors for both airflow and temperature. The VE is about twice more sensitive to air-jet pressure than NM, but sensitivity to coolness is about the same on both surfaces. The mechanoreceptors for airflow detection in VE or NM remain unknown, but likely candidates are proteins called TMC1/2 or Piezo2. TMC1/2 are transmembrane channel-like proteins present in stereocilia of hair cells that transduce changes in pressure, and thus generate neuronal signal information on flow. Piezo2 are large pressure-sensitive ion channels. The distribution of thermoreceptors in the nasal cavity was carefully studied by A S Jones et al., [The distribution of thermoreceptors within the nasal cavity. Clin Otolaryngol Allied Sci. 1989; 14(3):235-239] who emphasized the importance of the air-conditioning role played by these cool-sensing receptors in the compartments of the VE and NM. TRPM8 cooling channels are present in the nasal mucosa.

Skin, Keratinized Epithelia, and Permeation Barriers. There are four basic types of animal tissues: connective tissue, muscle tissue, nervous tissue, and epithelial tissue. Epithelia line ducts, cavities, and surfaces of organs throughout the body. When the epithelium is one cell layer thick, it is called simple epithelium. If there are two or more layers of cells, it is called stratified epithelium. Stratified epithelium is composed mainly of squamous (flattened) cells and some cuboidal cells. Historically, stratified epithelia divide into two broad categories: keratinized stratified epithelia, and non-keratinized stratified epithelia. Keratinized epithelium, such as the epidermis of the skin, has an exterior layer of dead cells [stratum corneum] composed of keratin proteins that are tough and water-impermeable. Keratin also covers the filiform papillae of the tongue. By contrast, non-keratinizing stratified epithelia do not contain a significant keratin layer and are present principally on the lining of the nasal cavity, portions of the oral cavity such as the inner lips, the pharyngeal surface, the esophageal surface, the lining of the respiratory tree, and the anogenital surface. The term "cornified epithelia" has traditionally been reserved for keratin-covered tissues such as nails, hair, and hooves [Bragulla and Homberger [Structure and functions of keratin proteins in simple, stratified, keratinized and cornified epithelia. Journal of Anatomy, 214: 516-59, 2009].

The surface skin of the nares and nasal vestibule is keratinized epithelia. As the skin of the nasal vestibule merges into the nasal cavity, it transits to a single layer of non-keratinizing respiratory epithelium. Transitional epithelia in the body are generally densely innervated with sensory nerve endings [e.g., the margins of the eyelids, the inner border of the lips, and the margins of the anogenitalia]. A layer of keratin is a barrier for drug access to neuronal receptive fields embedded in tissues underneath the keratin. Biologists now recognize keratin as a family of proteins that form integral filaments in the cytoskeleton of many cells. Hence, the term "non-keratinized stratified epithelia" is no longer accurate and may eventually become obsolete. The preferred term is "non-keratinizing stratified epithelia," implying that these cells do not form an external keratin layer. In the context of this application, the skin over the nostrils and nasal vestibule is "keratinizing stratified epithelia." This skin becomes transitional epithelia as it merges with the nasal vestibule and then becomes respiratory epithelia, which is non-keratinizing. Respiratory epithelium is a single cell layer known as pseudostratified epithelia.

TRP channels The transient receptor potential (TRP) family of cation channels are peripheral detectors of nociceptive and painful stimuli. Many are integral membrane proteins located on the nerve membranes of sensory neurons and respond to chemical irritants and changes in local temperature by activating nerve action potentials. The brain perceives these signals and react. The TRP receptors transduce sensory information, and this transduction and reflex system protects the organism from external irritants.

Thermosensory Mechanisms on the Skin One of the essential advances in physiology, in the past 20 years, is the discovery that physical changes such as heat, cold, and pressure are sensed and transduced by TRP integral membrane proteins on the cell surface. Typically, in an ambient environment of 18 to 25° C., the skin temperature remains constant at ~34° C. The thermoreceptor is in the extracellular fluid of the skin. The receptors coding for and transducing temperature belong to the TRP family of channel proteins. The receptive fields of the thermosensors for mask discomfort are in the trigeminal nerve (FIG. 12). These receptors sample static and dynamic changes in local temperature. TRPM8 nerve endings for cooling discretely aggregate in the body [Dhaka et al., vide supra]. The high density of nerves on the whisker pads of rodents is equivalent to the perioral areas of humans. Other sites are the nasal mucosa and lips.

Study 1
DIPA Compounds, Synthesis and Structures

The present discovery relates to certain compounds (the DIPA compounds described herein), which, when delivered onto the skin, selectively and potently evoke sensations of "dynamic cool" when applied to the skin. These compounds have applications in the treatment of face mask discomfort.

The structures of the preferred embodiments are shown below. The water-soluble compounds [e.g., 1-di-isopropyl-phosphinoyl-heptane] potently [<5 mg per dose] and rapidly produce on skin robust and intense cooling sensations. This type of drug action is unusual and has not been previously recognized as achievable on keratinized surfaces and has led to new applications, as described herein.

The DIPA compounds of the present discovery are achiral and are examples of 1-di-alkyl-phosphinoyl-alkanes [(O=)PR$_1$R$_2$R$_3$] wherein each of R$_1$, R$_2$, and R$_3$ is an alkyl group, and in particular where $R_1$ and $R_2$ are isopropyl, and $R_3$ is a linear alkyl group of 5 to 9 carbons, and which have the following general formula of Formula 1:

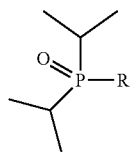

Formula 1 wherein R=n-pentyl, n-hexyl, n-heptyl, n-octyl, or n-nonyl

Chemical Synthesis

The DIPA compounds were prepared by the following general method: 100 mL (23.7 g, ~200 mmol) of isopropylmagnesium chloride (or sec-butylmagnesium chloride in the case of the di-sec-butyl derivatives) were obtained from Acros, as a 25% solution in tetrahydrofuran (THF) and placed under nitrogen in a 500 mL flask (with a stir bar). Diethyl phosphite solution in THF (from Aldrich, D99234; 8.25 g, 60.6 mmol in 50 mL) was added drop-wise. After approximately 30 minutes, the reaction mixture warmed up to boiling. The reaction mixture was stirred for an extra 30 minutes, followed by drop-wise addition of the appropriate n-alkyl iodide solution in THF (from TCI; 60 mmol in 20 mL). The reactive mixture was then stirred overnight at room temperature. The reaction mixture was diluted with water, transferred to a separatory funnel, acidified with acetic acid (~10 mL), and extracted twice with ether. The ether layer was washed with water and evaporated (RotaVap Buchi, bath temperature 40° C.). The light brown oil was distilled under a high vacuum. The final products, verified by mass spectrometry, were transparent liquids that were colorless. Professional chemists conducted synthesis at Phoenix Pharmaceuticals, Inc. (Burlingame, Calif.), Uetikon Laboratories (Lahr, Germany), and Dong Wha Pharmaceuticals (Seoul, Korea). Table 1 and 2 compounds were prepared by this general synthetic method and used for comparisons.

TABLE 1

DIPA compounds

| Code | Chemical Name | Formula/Weight | Chemical Structure |
| --- | --- | --- | --- |
| DIPA-1-5 | 1-di-isopropyl-phosphinoyl-pentane | $C_{11}H_{25}OP$ 204.32 | 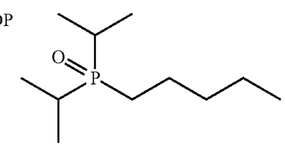 |
| DIPA-1-6 | 1-di-isopropyl-phosphinoyl-hexane | $C_{12}H_{27}OP$ 218.32 | 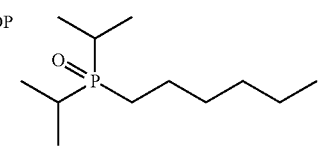 |
| DIPA-1-7 | 1-di-isopropyl-phosphinoyl-heptane | $C_{13}H_{29}OP$ 232.34 | 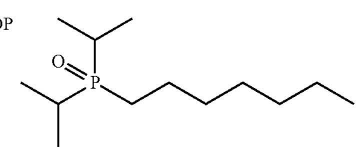 |
| DIPA-1-8 | 1-di-isopropyl phosphinoyl-octane | $C_{14}H_{31}OP$ 246.37 | 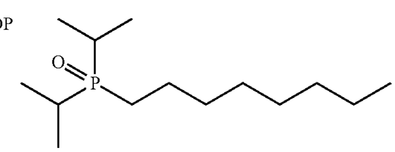 |
| DIPA-1-9 | 1-di-isopropyl phosphinoyl-nonane | $C_{15}H_{33}OP$ 260.40 | 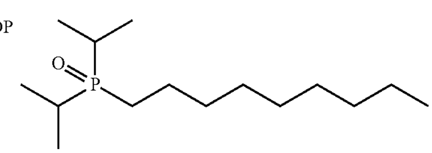 |

TABLE 2
Chemical structures of test compounds.
| Code | Chemical Name | Chemical Structure |
|---|---|---|
| 2-4 | 1-di(sec-butyl)-phosphinoyl-Butane | 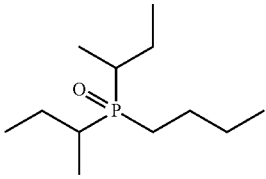 |
| 2-5 | 1-di(sec-butyl)-phosphinoyl-Pentane | 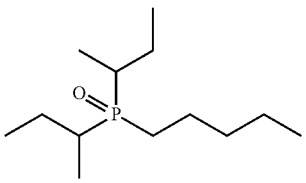 |
| 2-6 | 1-di(sec-butyl)-phosphinoyl-Hexane | 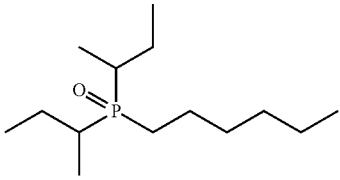 [SMILES: CCCCCCP(=O)(C(C)CC)C(C)CC] |
| 2-7 | 1-di(sec-butyl)-phosphinoyl-Heptane | 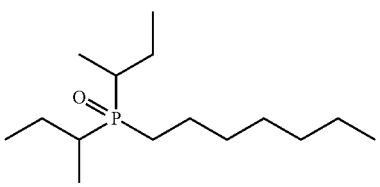 [SMILES: CCCCCCCP(=O)(C(C)CC)C(C)CC] |
| 2-8 | 1-di(sec-butyl)-phosphinoyl-Octane | 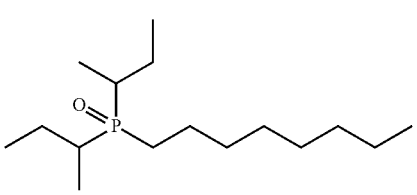 [SMILES: CCCCCCCCP(=O)(C(C)CC)C(C)CC] |
| 3-1 | 1-di(iso-butyl)-phosphinoyl-Pentane | 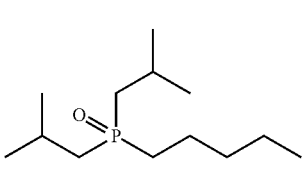 |
| 3-2 | 1-di(sec-butyl)-phosphinoyl-3-methyl-butane | 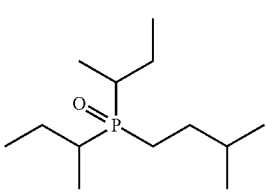 |

TABLE 3

Chemical structures of "Mixed" test compounds.

| | | |
|---|---|---|
| 3,4-6 | 1-isopropyl-sec-butyl-phosphinoyl-hexane | |
| 3,4-7 | 1-isopropyl-sec-butyl-phosphinoyl-heptane | |

The 3,4-X series are "mixed" isopropyl-sec-butyl compounds (Table 3). These were synthesized by Dr. Jae Kyun Lim of Dong Wha Pharmaceuticals, using the method described below.

Briefly, as illustrated in the following scheme, triethyl phosphite (A) was reacted with sec-butyl magnesium bromide (B) and then hydrolyzed with dilute hydrochloric acid to give the mono-alkyl compound (C). The product (C) was then reacted isopropyl magnesium bromide (D) to give the di-alkyl compound (E), which was then reacted with a suitable alkyl iodide (F) to give the target trialkyl phosphine (G).

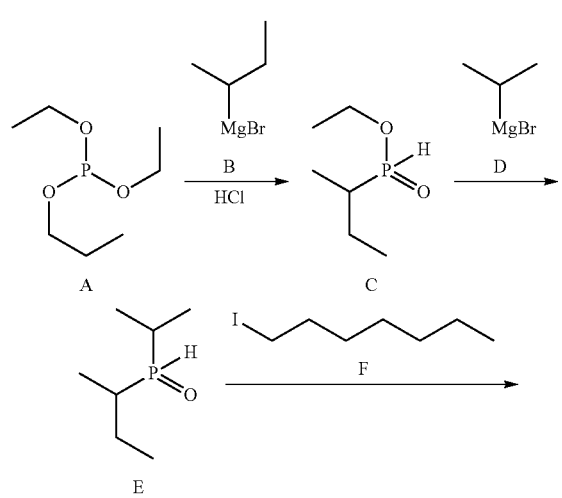

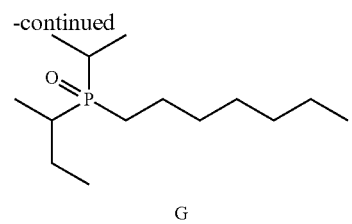

General Observations of Properties

DIPA compounds are colorless liquids with a density less than water. The preferred embodiments DIPA-1-5, DIPA-1-6, DIPA-1-7, DIPA-1-8, and DIPA-1-9 exert an icy sensation on epithelia that is modulated by dose, formulation, and method of delivery. Similar structures were described by Rowsell and Spring U.S. Pat. No. 4,070,496 (1978) ~40+ years ago but have remained dormant in the scientific literature. The '496 structures all have their "head" (phosphine oxide group) covered by larger, more lipophilic groups. The applicant noted that '496 did not include the di-isopropyl analogs. The applicant synthesized these analogs (which are achiral, by contrast to the structures of '496, which are >95% chiral). The applicant found that, by minimizing the two alkyl side chains to di-isopropyl, the "head" of the prototypical molecule now is more polar (hydrophilic) and more miscible in the polar environment of water. This increased water-solubility is striking (Table 4). The water solubility of the DIPA if at least 10× more than the di-sec-butyl or the mixed isopropyl-sec-butyl analogs. The DIPA analogs are now mobile in the extracellular fluids and permeate between cells to access nerve endings in the stratum basale.

TABLE 4

Water solubility (mg/ml) of 1-dialkylphosphorylalkanes ($R_1R_2R_3P = O$).

| | No. Carbons | | | | | | | |
|---|---|---|---|---|---|---|---|---|
| | 13 | | 14 | | 15 | | 16 | |
| $R_1, R_2$ | $R_3$ | | $R_3$ | | $R_3$ | | $R_3$ | |
| di-sec-butyl- | pentane | 22 | hexane | 8 | heptane | <3 | octane | <3 |
| isopropyl-sec-butyl- | hexane | 25 | heptane | 20 | octane | <3 | nonane | <3 |
| di-isopropyl- | heptane | >300 | octane | >300 | nonane | >300 | decane | <3 |

Facial application of DIPA compounds as an aqueous solution at 1-10 mg/mL or a 1% hydrogel, is non-irritating. For certain analogs, contacting the skin with a solution at a concentration of 1 to 10 mg/mL produces a sensation of "dynamic cool," which occurs within one minute after application. DIPA-1-7, especially, has intense dynamic cooling.

Compositions

In one embodiment, the composition comprises the DIPA compound at a concentration of 0.05 to 2.0% wt/vol. In one embodiment, the composition is a liquid or semi-liquid composition (gel, lotion, cream, or ointment), and comprises the DIPA compound at a concentration of 0.5 to 20 mg/mL. In one embodiment, the composition is a liquid rinse and comprises the DIPA compound at a concentration of 0.05 to 0.25 mg/mL in water or isotonic saline. In one embodiment, the composition is a gel and comprises the DIPA compound at a concentration of 5 to 25 mg/mL in water and 0.5% of a Carbopol gel.

The composition may be provided with suitable packaging and in a suitable container. For example, the composition may be as a rinse, swab, wipe, pad, or towelette (e.g., suitably sealed in a wrap) carrying a DIPA compound or a composition comprising a DIPA compound. In another example, the composition is provided as a solution in a single unit dispenser, e.g., in a volume of 1 mL per dispenser, for example, as manufactured by Unicep Corporation (1702 Industrial Drive, Sandpoint, Id., USA)

In one embodiment (e.g., of use in methods of therapy, of use in the manufacture of medicaments, of methods of treatment), the treatment is the treatment of sensory discomfort caused by wearing a face mask. The term "sensory discomfort", as used herein, relates to unpleasant sensations from the facial surface such as difficulty in breathing, suffocation, dyspnea, or heat. It is presumed that nociceptors are stimulated, for example, by high temperatures or air stasis of a face mask. A DIPA compound, such as DIPA-1-6 or DIPA-1-7 alleviates sensory discomfort and is therefore termed an anti-nociceptive agent. In one embodiment, the treatment conveys a sense of refreshment to the facial skin in a human.

For a liquid vehicle or semi-liquid vehicle, a preferred delivered volume is 0.05 to 2.0 mL. Such a volume, delivered for example as a solution, gel, lotion, or a wipe, does not cause much residual liquid at the delivery site, as is absorbed onto the skin. For a liquid vehicle, a preferred concentration of the DIPA compound is in the range of 0.5 to 30 mg/mL. For the facial skin, a preferred concentration is 1 to 15 mg/mL. For the zygomatic and infraorbital skin, a preferred concentration is 5 to 10 mg/mL. A preferred amount of the DIPA compound delivered at the site of the application is 0.1 to 5 mg; for example, 0.1 to 5 mg.

Delivery of the DIPA compound on the target skin with a swab can be done with a dispenser and a plastic or cotton-tipped applicator, and are well-known in personal care products. Alternatively, a polyethylene bulb applicator may also be used. These gel packs can be a single-use sealed unit or in a multi-unit dispenser. For single units, suitable wrapper materials are relatively vapor impermeable, prevent drying out of the wipe, and form a "peelable" seal. Examples of suitable wipe materials for practicing this discovery include polyamide (20% Nylon)-polyester, rayon (70%)-polyester (30%) formed fabric, polypropylene nonwoven, polyethylene terephthalate (PET), polyester polypropylene blends, cotton, viscose, rayon, or microfibers (synthetic fibers that measure less than one denier or one decitex).

Alternatively, a solution containing a DIPA compound is in a reservoir bottle with individual applicators, or as a pre-packaged individual unit. For example, Puritan 803-PCL applicators are ideal cotton-tipped applicators attached to a 3-inch (~7.5 cm) polystyrene rod for delivery of a DIPA compound onto the nasal skin. Examples of applicators individually packaged are the SwabDose™ from Unicep Corporation (1702 Industrial Drive, Sandpoint, Id., USA). Each applicator tip is saturated by dipping the absorbent material of the tip (e.g., 40 to 100 mg of cotton) in 0.1 to 1.5 mL of an aqueous or gel solution of a DIPA compound and packaged in an individual container.

Selection of Active Ingredient

An active pharmaceutical ingredient (API) for delivery to the face's keratinized skin should be stable, non-toxic, and long-acting. The API should potently activate the mechanisms that result in the relief of face mask discomfort. The API should dissolve and evenly disperse in a composition so that during manufacture, the formulation maintains a constant concentration. The final product should meet the standards of cleanliness and sterility. For formulation, the API can be a liquid at standard conditions of temperature and pressure (STP). It should dissolve in aqueous solutions at neutral pH and isotonicity. The final product is sterile by using purified reagents and micropore filters, heating, or irradiation. Standard solvents such as water or isotonic saline, stabilizing agents, and preservatives, may be added to optimize the formulations, but the essential ingredients should be preferably soluble in aqueous media such as purified water or a standard dermatological solvent. The DIPA compounds meet these criteria.

For a given individual, the perceived sensation is a function of the particular cooling agent, the dose, the vehicle used to carry the cooling agent, the method of topical delivery, and the nature of the target surfaces. The applicant has screened many candidates on the facial skin (Wei. Sensory/cooling agents for skin discomfort. Journal Skin Barrier Research 14: 5-12, 2012). The studies here identify preferred DIPA compounds with properties of an ideal agent for the relief of face mask discomfort.

Study 2

General Parameters of Sensory Effects of Compounds on Facial Skin

Compounds tested on the skin produce a characteristic pattern of sensations. The quality of cooling sensations evoked, their descriptors, and their proposed mechanism of action, are summarised in Table 5. For each compound, there is usually only one or two categories of overlapping sensations. For example, icilin is exclusively cool, with very little "cold." DIPA-1-6 and DIPA-1-7 produce a robust "dynamic cool" that can elicit "stinging" sensations at higher concentrations. DIPA-1-8 and DIPA-1-9 are potent cold-producing agents.

TABLE 5

Descriptor and proposed mechanisms of DIPA compounds on skin.

| Type of Sensation | Descriptor | Proposed Mechanisms on Sensory Neurons |
| --- | --- | --- |
| Inactive | No effect | — |
| Cool, steady and pleasant | Cool | Balanced stimulation of static and dynamic units. |
| Cold, constant | Cold | Higher stimulation of static units. |
| Dynamic cooling, robust cool/cold, strong refreshing | Dynamic cool | Higher stimulation of dynamic units. |
| Stinging cold, sometimes with irritation | Icy cold | Stimulation of dynamic and static units, and also nociceptive sites |

After the offset of the cooling/cold action, some compounds have a "reservoir effect." Experimentally, this is measured 1 hour after an offset by placing a hot towel over the site of application and determining if the onset of cooling/cold returns for at least 15 minutes. If this occurs, then there is a definite "reservoir effect." The "reservoir effect" can also be provoked with air movement, but the conditions for air movement are difficult to standardize. A hand held minifan can be used. The "reservoir effect" of DIPA-compounds in the skin is most likely due to residual drug deposited in the skin, which reactivates to stimulate dynamic/static sensory neurons. In this context, the anterior has a subcutaneous layer of fibro-fatty tissue that may serve as a drug reservoir.

Figure 4:
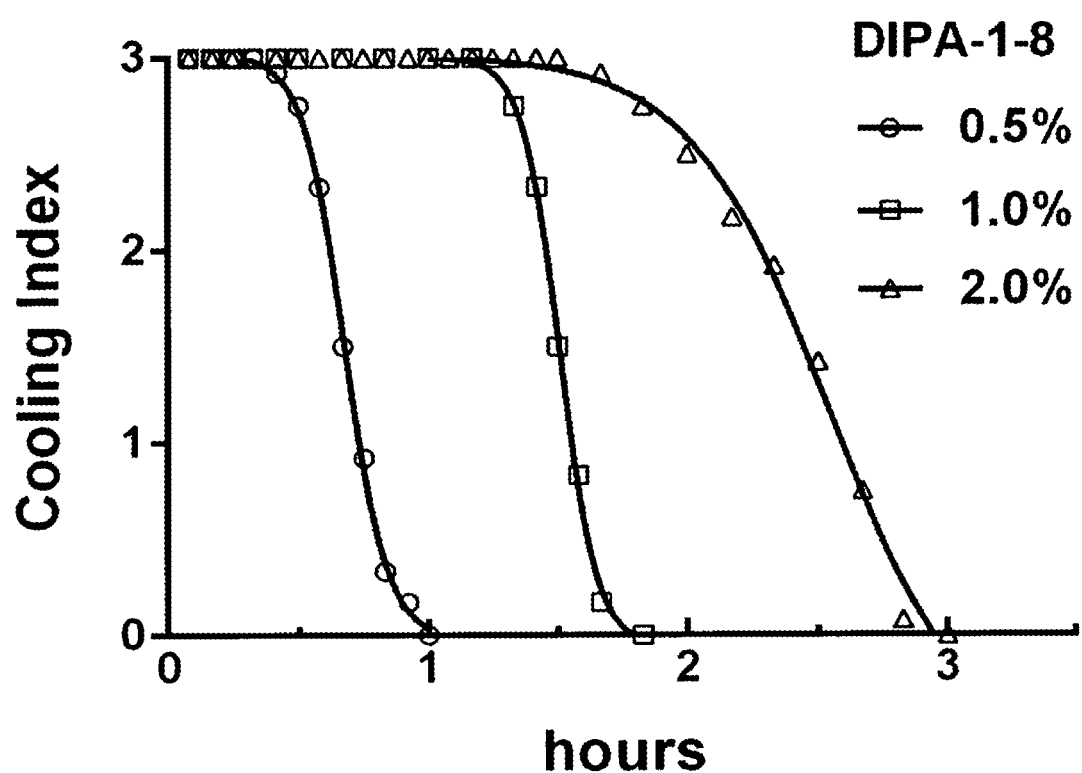
FIG. 4. shows the cooling sensations evoked by topical wiping of different concentrations of DIPA-1-8, a TRPM8 agonist, onto the skin above the zygomatic process. The cooling activity can be measured as the intensity/duration area-under-curve (AUC) or as the time for half-maximal effect ($T_{-1/2}$), using software of the GraphPad Prism package. The graph shows the dose-response curve for the compound DIPA-1-8 applied at 0.5, 1, and 2% (5, 10, and 20 mg/mL dissolved in distilled water).

In the studies described herein, the sensation of coolness/cold is rated as 0, 1, 2, or 3 with 0 as no change; 1 as mild coolness; 2 as clear-cut signal of coolness; and 3 as robust cooling. The sensations are recorded at intervals of 5 to 15 minutes until two consecutive zeroes. The test results for DIPA-1-8 on the zygomatic skin is shown in FIG. 4. The onset of drug action is taken as the time to reach 2 units of coolness intensity. The duration of sensory action is defined as the offset time minus the onset time. An inactive compound is defined as one that does not exceed 2 units of cooling for 5 minutes or more after application. The offset endpoint is sometimes unstable for compounds that act for two or more hours, because the coolness/cold sensation may fluctuate due to environmental variables such as sunlight, ventilation, activity, and the "reservoir effect." The summarized effects of various analogs are shown on FIG. 5. These results and methods have also been published in U.S. Ser. No. 16/350,559, filed Nov. 30, 2020, and are hereby incorporated by reference.

Tables 6 show the effects of test compounds on zygomatic facial skin. Test compounds were applied 20 mg/mL in distilled water to the skin of the zygoma using cotton gauze (0.4 g, rectangular, 50 mm×60 mm; from CS-being, Daisan Cotton, Japan). The onset and duration of the sensory effect was measured with a stopwatch. The degree of "dynamic cool" was graded from 0 to +++, with intermediate steps of + and ++.

Quarter and half-point scores are allowed. The scoring stopped when two consecutive zeroes occurred in a 10 min interval. Two to three volunteers was used for each compound. Results from the testing of DIPA-1-8 at three concentrations are shown in FIG. 4

FIG. 4. shows the cooling sensations evoked by topical wiping of different concentrations of DIPA-1-8 onto the skin above the zygomatic process. The cooling activity can be measured as the intensity/duration area-under-curve (AUC) or as time for half maximal effect ($T_{-1/2}$), using software of the GraphPad Prism package. The graph shows the AUC dose-response curve for the compound DIPA-1-8 applied at 0.5, 1 and 2% (5, 10, and 20 mg/mL dissolved in distilled water).

Figure 6:
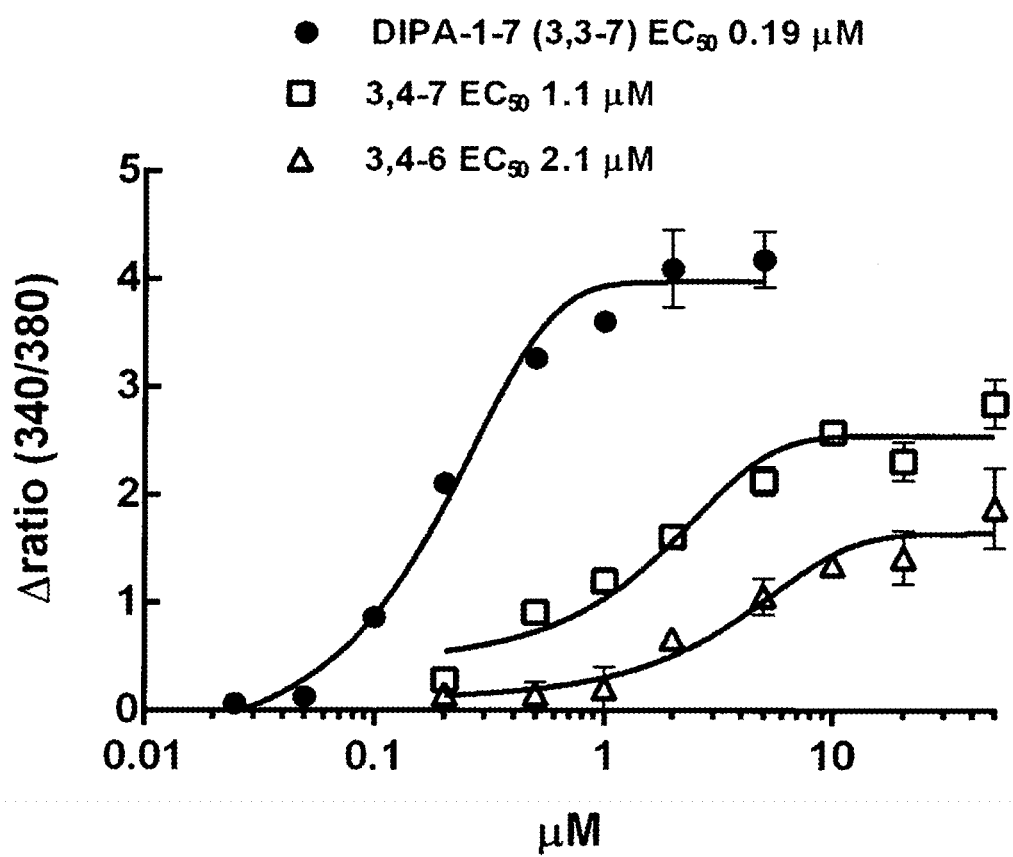
FIG. 6. is a graph of fluorescence response (A ratio 340/380) in TRPM8 transfected cells as a function of the logarithm of the concentration of the test compound, expressed in µM, for DIPA-1-7 (black circle), 3,4-7 (open squares), or 3,4-6 (open triangles). The assays were conducted by Andersson et al. of King's College, London, UK, using his methods described in "Modulation of the cold-activated channel TRPM8 by lysophospholipids and polyunsaturated fatty acids. Journal Neuroscience 27 (12): 3347-3355, 2007.

A comparison of the DIPA diisopropyl analogs (3,3-X) versus the mixed propyl-sec-butyl analogs (3,4-X) are shown in FIG. 6. Statistical significant differences (P<0.01) are seen between 3,3-x and the asymmetrical chiral 3,4-x analogs. The 3,4-8 and 3,4-9 formed a milky/small oil droplet emulsion at 20 mg/mL and were not tested further in this study. Notably, DIPA-1-7 selectively produced the unusual sensation of "dynamic cool." From the data shown above, it was apparent that DIPA-1-7 evoked "dynamic cool" on both periorbital and zygomatic/forehead surface. Another compound with similar properties was DIPA-1-8, The long duration of action of DIPA-1-8 and DIPA-1-9 on the skin adds value as an agent for the treatment of mask discomfort. As shown in the case studies described below, a single application of DIPA-1-7 or DIPA-1-8 is sufficient to counteract mask discomfort for at least three to four hours. The exceptional value of DIPA-1-7 is the immediate comfortable cooling it provides. The advantages of DIPA-1-9 is its long duration of action after application onto the nostril skin and the absence of any stinging. Thus, it has an essential therapeutic niche for the relief of face mask discomfort. These results for the particular attributes of the DIPA

TABLE 6

Sensory effects after application to zygomatic and forehead skin.

| Code | $R_3$ | Carbon atoms | Onset (min) | Sensory Quality | Anti-Fatigue | Duration (hr) | Reservoir Effect |
|---|---|---|---|---|---|---|---|
| DIPA-1-5 | 5 | 11 | ~1 | dynamic | 0 | 0.5 | No |
| DIPA-1-6 | 6 | 12 | ~1 | dynamic | ++ | 1.3 | Yes |
| DIPA-1-7 | 7 | 13 | ~1 | dynamic-icy | +++ | 3.2 | Yes |
| DIPA-1-8 | 8 | 14 | ~1 | cold-icy | ++ | 4.0 | Yes |
| DIPA-1-9 | 9 | 15 | ~2 | cool | 0 | 2.0 | No |
| 2-4 | 4 | 12 | ~1 | cool | 0 | 0.3 | No |
| 2-5 | 5 | 13 | ~1 | cool | 0 | 1.1 | Yes |
| 2-6 | 6 | 14 | ~2 | cold | + | 1.5 | Yes |
| 2-7 | 7 | 15 | ~2 | cold | + | 2.4 | Yes |
| 2-8 | 8 | 16 | 5 | cold | 0 | 5.6 | Yes |

Each of 3-1 and 3-2 was tested and found to be inactive on periorbital, and zygomatic/forehead skin.

Figure 5:
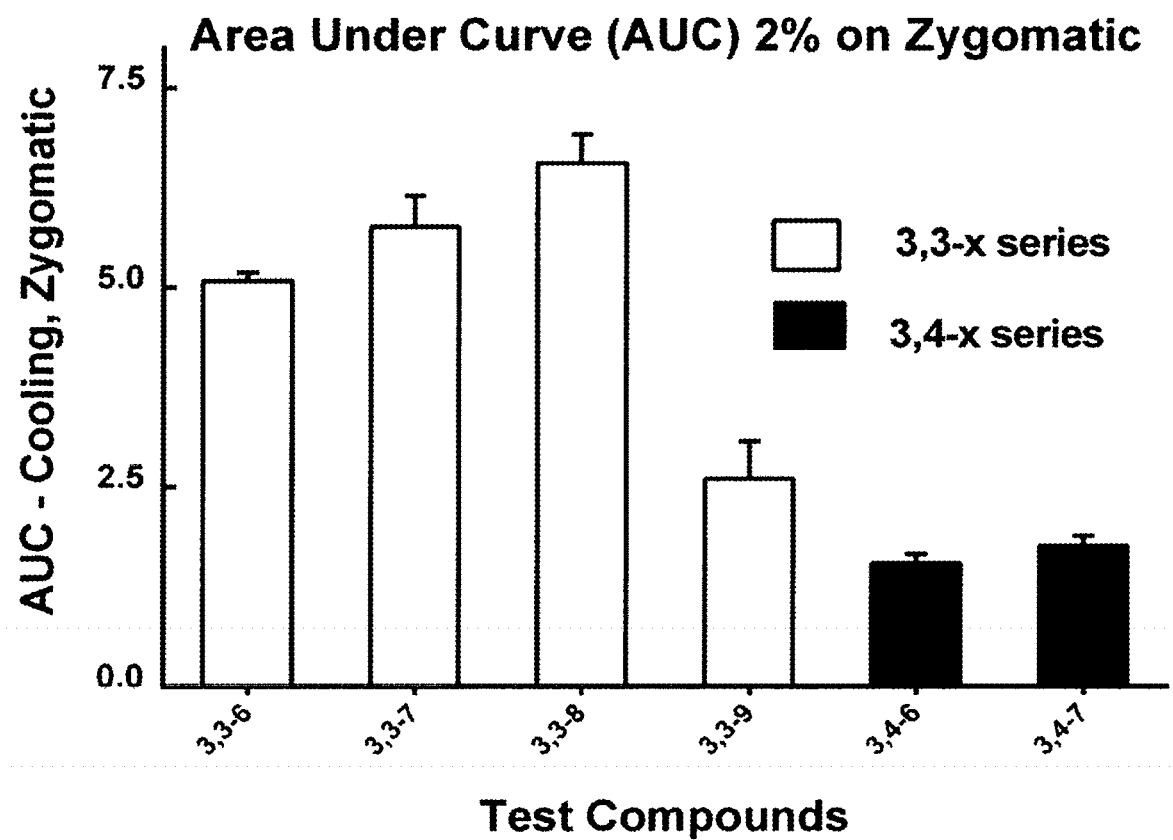
FIG. 5. shows the cooling sensations evoked by the topical wiping of different compounds onto the skin above the zygomatic process. The cooling activity is expressed as the integrated intensity/duration area-under-curve (AUC), using the software of the GraphPad Prism package. Test concentration was 2% (20 mg/mL in distilled water). The diisopropyl analogs are DIPA 3,3-X and isopropyl, sec-butyl analogs are Mixed 3,4-X. The "X" refers to the number of carbons on the third alkyl group. The Mixed analogs are much less active on the cheekbone skin than the corresponding diisopropyl analogs.

For further comparisons, the newly synthesized "Mixed" 1-isopropyl-sec-butyl-phosphorylalkanes (3,4-6, 3,4-7, 3,4-8, and 3,4-9) were tested on zygomatic skin (FIG. 5). The test procedures were modified because of the limited quantities of these analogs. To deliver the solution to the skin, an 80%-polyester-20%-viscose rayon wipe was cut into squares (7×8 cm, 0.45 g each) and a precise volume (2.5 mL) of test solution added to the wipe using a dropper bottle. An average 74±2 µL volume containing the test ingredient was wiped onto the receptive fields of the nerves on the zygomatic process (cheekbone). As before, the sensory effects of cool/cold were recorded at 5 and 10 min intervals.

preferred embodiments are unexpected, surprising, and have practical applications for counteracting face mask discomfort.

The selection of the best DIPA compound for face masks may depend on conditions of use. Face masks relief is preferable with a short-acting robust cooling agent such as DIPA-1-7 or DIPA-1-8, and relief of N-95 respirator discomfort may be preferable with DIPA-1-9 which is longer-acting.

Study 3
Receptor Agonist Activity of Compounds on TRPM8

The in vitro effects of the first set of test compounds (Table 1 and 2) were evaluated on cloned hTRPM8 channel (encoded by the human TRPM8 gene, expressed in CHO cells) using a Fluo-8 calcium kit and a Fluorescence Imaging Plate Reader (FLIPR$^{TETRA\text{™}}$) instrument (conducted by ChanTest Corporation (14656 Neo Parkway, Cleveland, Ohio 44128, USA). Test compounds and positive control solutions were diluted stock HEPES-buffered physiological saline (HBPS) solutions. The test and control formulations were loaded in polypropylene or glass-lined 384-well plates, and placed into the FLIPR instrument (Molecular Devices Corporation, Union City, Calif., USA). Tests were 4 or 8 concentrations with n=4 replicates per determination, and the positive control reference compound was L-menthol, a known TRPM8 agonist. The test cells were Chinese Hamster Ovary (CHO) cells stably transfected with human TRPM8 cDNAs.

For FLIPR$^{TETRA\text{™}}$ assay, cells plated in 384-well black wall, flat clear-bottom microtiter plates (Type: BD Biocoat Poly-D-Lysine Multiwell Cell Culture Plate) were approximately 30,000 cells per well. Cells were incubated at 37° C. overnight to reach a near confluent monolayer appropriate for use in a fluorescence assay. The test procedure was to remove the growth media and to add 40 μL of HBPS containing Fluo-8 for 30 minutes at 37° C. 10 μL of the test compound, vehicle, or control solutions in HBPS were added to each well and read for 4 minutes. Concentration-response data were analyzed via the FLIPR Control software that is supplied with the FLIPR System (MDS-AT) and fitted to a Hill equation of the following form:

$$\text{RESPONSE} = \text{Base} + \frac{\text{Max} - \text{Base}}{1 + \left(\frac{xhalf}{x}\right)^{rate}}$$

where: "Base" is the response at low concentrations of a test compound; "Max" is the maximum response at high concentrations; "xhalf" is the $EC_{50}$, the concentration of test compound producing half-maximal activation; and "rate" is the Hill coefficient. Nonlinear least-squares fits were assumed based on a simple one-to-one binding model. The 95% Confidence Interval was from the GraphPad Prism 6 software. The results summary is in Table 7. These results are fully described in Yang et al. (vide supra).

Figure 7:
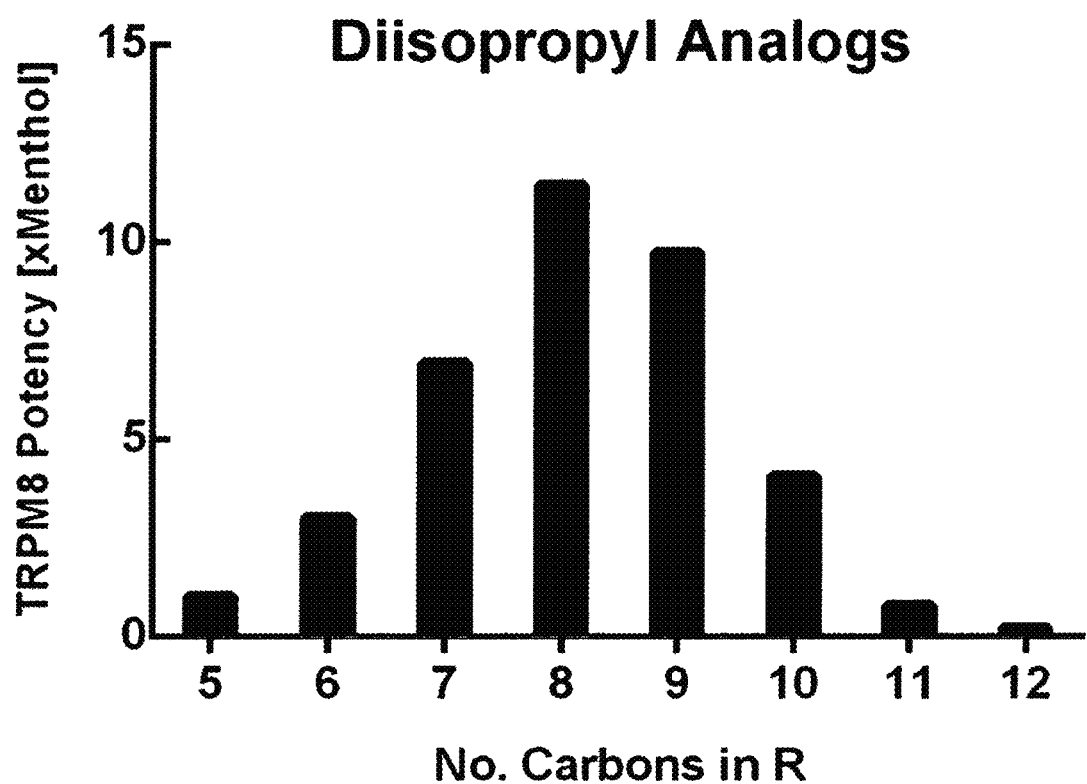
FIG. 7. is a graph showing the potencies of 1-diisopropylalkanes on the TRPM8 receptor assay. On the ordinate, potency is shown relative to 1-menthol. On the abscissa, the number of carbons in the n-alkane is enumerated.

The $EC_{50}$ of the more potent compounds (DIPA-1-7, DIPA-1-8, DIPA-1-9) fell within a narrow range with overlapping 95% Confidence Intervals (FIG. 7, Table 7). The potency of DIPA-1-7, DIPA-1-8, and DIPA-1-9 are similar and significantly higher than the potencies of DIPA-1-5 and DIPA-1-6. The structural modifications of related compounds 3-1 and 3-2 resulted in a significant loss of bioactivity. Further studies examined the specificity of the test compounds on TRPV1 channels (human TRPV1 gene expressed in HEK293 cells) and TRPA1 channels (human TRPA1 gene expressed in CHO cells). The test cells were Chinese Hamster Ovary (CHO) cells or HumanE embryonic Kidney (HEK) 293 cells transfected with human TRPV1 or TRPA1 cDNAs. The preferred embodiments show selective activity on TRPM8 and not on TRPA1 or TRPV1 (see Yang et al. vide supra).

TABLE 7

| | $EC_{50}$ and relative potency of compounds on TRPM8. | | |
|---|---|---|---|
| Code | $EC_{50}$ μM | 95% Confidence Interval | Relative Potency |
| Menthol | 3.8 | 2.5 to 5.6 | 1.0 |
| DIPA-1-5 | 5.6 | 4.4 to 7.2 | 0.7 |

TABLE 7-continued

| | $EC_{50}$ and relative potency of compounds on TRPM8. | | |
|---|---|---|---|
| Code | $EC_{50}$ μM | 95% Confidence Interval | Relative Potency |
| DIPA-1-6 | 2.4 | 1.5 to 4.0 | 1.6 |
| DIPA-1-7 | 0.7 | 0.5 to 1.0 | 5.4 |
| DIPA-1-8 | 0.7 | 0.5 to 1.0 | 5.4 |
| DIPA-1-9 | 0.9 | 0.4 to 2.5 | 4.0 |
| 2-4 | 14.5 | 7 to 29 | 0.3 |
| 2-5 | 1.7 | 1.0 to 2.9 | 2.2 |
| 2-6 | 0.8 | 0.5 to 1.3 | 4.7 |
| 2-7 | 1.1 | 0.6 to 2.3 | 3.4 |
| 2-8 | 1.3 | 0.7 to 2.3 | 2.9 |
| 3-1 | 24 | 8 to 76 | 0.2 |
| 3-2 | 4.2 | 1.6 to 10.8 | 0.9 |

Of the 12 compounds tested, all showed full efficacy on the TRPM8 receptor, i.e., at higher tested concentrations, there was ~100% stimulation of calcium entry, and the data fitted a sigmoidal dose-response curve. The results for the "di-isopropyl" compounds of this invention are illustrated in FIG. 7.

Selectivity tests were conducted on Human Embyronic Kidney (HEK) 293 cells transfected with human TRPV1 or TRPA1 cDNAs. The positive control reference compound was capsaicin (a known TRPV1 agonist) or mustard oil (a known TRPA1 agonist). DIPA-1-7 and DIPA-1-8 did not exhibit any agonist on antagonist activity on TRPA1 channels at maximum tested concentrations of 100 μM. DIPA-1-7 had a weak TRPV1 agonist activity, but this was not dose-dependent.

Further tests were conducted on "mixed" isopropyl-sec-butylphosphorylhexane and heptane analogs. The data were collected by Andersson et al. of King's College, London, UK, using his methods described in "Modulation of the cold-activated channel TRPM8 by lysophospholipids and polyunsaturated fatty acids. Journal Neuroscience 27 (12): 3347-3355, 2007. Here, the cellular entry of the calcium-sensitive dye Fura-2 was used to study the effect of the test compounds on TRPM8 expressed in Chinese hamster ovary cells. Cells, grown in culture, were seeded at an approximate density of 30,000 cells/well overnight and loaded for ~1 hr with 2 M Fura-2 (Molecular Probes, Leiden, The Netherlands), and then placed on glass coverslips. Test solutions were added with a micropipette positioned close to the cells. Emission intensity from cells was measured for 90 sec, at every 4 or 5 sec, using excitation wavelengths of 340 and 380 nm and an emission of 520 nm. Fluorescence emission intensity ratios at 340 nm/380 nm excitation (R, in individual cells) were recorded with a FlexStation and the ImageMaster suite of software (PTI, South Brunswick, N.J.). Samples were tested in triplicate at each concentration and the averaged values analyzed by nonlinear regression using a sigmoidal function fit of the points to obtain an estimated EC50 (median effective concentration) (GraphPad Prism software, La Jolla, Calif.).

The potency of three analogs for activation of TRPM8 (cooling receptor) in transfected cells is shown in FIG. 6. The units (A ratio) on the ordinate measures entry of fluorescent calcium probes into transfected cells. The 3,3-7 (DIPA-1-7) is substantially more potent (~10× and ~5×) than 3,4-6 and 3,4-7. Note that 3,4-6 and 3,4-7 species do not reach the same degree maximal efficacy on activation of the receptor, even at supra-maximal concentrations. From these results, it appears that the $EC_{50}$ values do not give robust information on the quality of the heat abstraction sensation, the duration of action, or the accessibility of the molecule to tissue targets. The identification of selective agents required development of more in vivo bioassays to directly address these questions.

FIG. 6. is a graph of fluorescence response (Δ ratio 340/380) in TRPM8 transfected cells as a function of the logarithm of the concentration of the test compound, expressed in μM, for DIPA-1-7 (black circle), 3,4-7 (open squares), or 3,4-6 (open triangles). The assays were conducted by Andersson et al. of King's College, London, UK, using his methods described in "Modulation of the cold-activated channel TRPM8 by lysophospholipids and polyunsaturated fatty acids. Journal Neuroscience 27 (12): 3347-3355, 2007.

Study 3
Transdermal Activity of Preferred Embodiments

The receptor targets on nerve endings embed and interdigitate in the epithelial cell layers. The epidermis is only ~1 mm thick, but dead cell layers (stratum corneum) of denatured proteins impede access of the agonist molecule to the nerve endings. The heel of the feet is the thickest barrier, 86 cell layers for the heel, and followed by the palm, then the back of the hand. If you put an ice cube on the heel, you feel a bit of cold: but you jump when you put it on the sole of the feet, which has fewer layers. Unless the skin of the thick surfaces is structurally damaged (e.g., by inflammation) applying a cooling agent does not work, because the molecules do not access the nerve endings. For other surfaces, the genital skin (glans of the penis and vulva) and the eyelids are the thinnest, with 4 to 8 cell layers. The extremities, arms and legs, and the trunk (back) have thick surfaces. The scalp is intermediate. The face varies: the lateral cheek is relatively insensitive, but areas around the orbit and nasolabial folds are thin and sensitive. I estimate that the cell layer thickness for the cheek is 15 to 18 cell layers, and 7 to 15 cell layers for the nostrils, nasal vestibule, philtrum, alar crease, nasolabial folds, vermillion, and chin. These differences are critical for drug action! For cooling to relieve mask discomfort, one must choose the molecule carefully to get the desired effects, avoid too much stimulation and exert gentle cooling.

The applicant's preferred embodiments of DIPA-1-7, DIPA-1-8, and DIPA-1-9, wherein two of the alkyl groups (e.g., $R_2$ and $R_3$) are both isopropyl, have high water solubility and adequate skin penetration. Increasing water solubility to increase bioactivity is counterintuitive, as in standard drug design, the desire is to increase lipid solubility to enhance transdermal drug permeation. Usually, formulation experts try to break down the stratum corneum with enhancers, and chemists try to increase lipid solubility of the molecule (see, e.g., M. Prausnitz et al. Skin barrier and transdermal drug delivery. Chpt. 124, Medical Therapy, 2012). The alternative strategy used here was, however, met with clinical success.

To further study the skin permeation of DIPA compounds, we tested the indirect flux of DIPA-1-5 to DIPA-1-9 through rat skin, using an in vivo assay. The results showed that DIPA-1-5, DIPA-1-6, and DIPA-1-7 evoke robust shaking, indicative of transdermal penetration in vivo, but this is not seen with other analogs. This is an unusual and surprising observation and indicates that these structures, perhaps because of smaller molecular size, can penetrate the stratum corneum of keratinized skin. Other studies of transdermal penetration in excised mouse skind models are described in U.S. Ser. No. 16/873,626, of which this application is a continuation-in-part.

Figure 8:
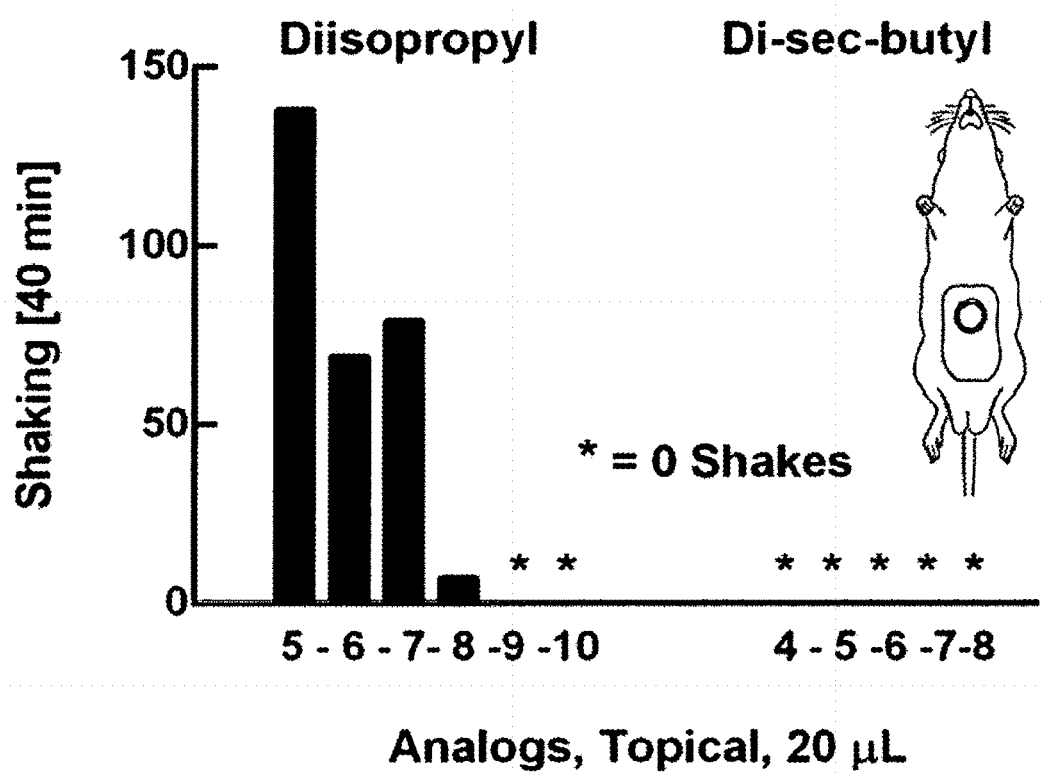
FIG. 8. shows the method for estimating the in vivo transdermal activity of the DIPA-embodiment compounds applied 20 µL with a micropipette to the center of a circle enclosed by cream on abdominal skin of an anesthetized rat. Shaking frequency was counted for 40 min after topical application. It can be seen that the embodiments DIPA-1-5, DIPA-1-6, and DIPA-1-7 evoke robust shaking, but this is not seen with other analogs.

FIG. 8. shows the method for estimating the in vivo transdermal activity of the DIPA-embodiment compounds applied 20 μL with a micropipette to the center of a circle enclosed by cream on abdominal skin of an anesthetized rat. Shaking frequency was counted for 40 min after topical application. It can be seen that the embodiments DIPA-1-5, DIPA-1-6, and DIP-1-7 evoke robust shaking, but this is not seen with other analogs.

Standard enhancers with polyhydric alcohols, such as a propylene glycol-oleyl alcohol mixture (50:50) or Lauroglycol 90, designed to increase permeation added to the 1-7 gel decreased the rate of permeation by ~50%, indicating the importance of water solubility for permeation (U.S. Ser. No. 16/873,626). In studies on the abdominal skin of anesthetized rats, a 50:50 propylene glycol-DIPA-1-7 mixture was inactive when tested on the skin of animals, with shaking as an endpoint, whereas the pure DIPA-1-7 was very active. Thus, standard solvents or enhancers of dermatological molecules impede rather than facilitate passage of the DIPA through the skin barriers. The mobility of the DIPA molecules in an aqueous environment through a skin barrier is unusual and surprising. The "unmasking" of the polar "head" by one or more carbon (e.g., methyl) groups, increases water solubility and permeability. The symmetrical (achiral) arms (the isopropyl groups) may also enable efficient swimming of the DIPA through the pores of the stratum corneum and into the extracellular fluid to reach the TRPM8 receptors in the stratum basale.

The results in Study 3 show that the DIPA compounds can penetrate keratinized skin and therefore will be active when applied to the keratinized skin of the nostrils and nasal vestibule.

Study 4
Identification of Target Sites for Face Mask Discomfort: Anatomical Localization A standard N95-FFR mask covers the skin over the bridge of the nose, the cheeks, the mouth, and the chin. The triangular area enclosed by the nasolabial folds (smile lines), alar crease, the nostrils, vermilion, and the lower lip, is sensitive to heat. The tip and dome of the nose and the skin of the nares sense air temperature and humidity. In the respiratory epithelium, within the nasal cavity, receptive fields are present, especially around Kiesselbach's plexus (Little's area, see Zhao et al., vide supra). The cranial nerves transmit somatosensory and thermosensory signals from the face, nasal cavity, and mouth. The facial signals are highly integrated into temperature regulation, as exemplified by the observation that cooling of the face is two to five times more effective at suppressing sweating and thermal discomfort than cooling an equivalent skin area elsewhere on the body (Cotter and Taylor, vide supra).

The head is known to be a site where cooling helps relieve heat discomfort. Nakamura et al. [2013. "Relative Importance of Different Surface Regions for Thermal Comfort in Humans." European J. Appl. Physiol. 113: 63-76] exposed eleven male subjects to mild heat. Subjects, clothed in only short pants, entered a climatic chamber maintained at 32.5±0.5° C. with a relative humidity of 50%. About 1.5 hours after entry into the chamber, a local cooling protocol was initiated with water-perfused stimulators placed on the head, chest, abdomen, or thigh. The subjects felt cooling of the face and thigh was more effective than cooling of the chest and abdomen in reducing the heat discomfort.

Essick et al. [Site-dependent and subject-related variations in perioral thermal sensitivity. Somatosensory Motor Research 21, 159-75, 2004] measured the thresholds for detecting cooling and cold pain on various sites of the face, ventral forearm, and scalp for 34 young adults. On the face, the most sensitive sites were on the vermilion, which could detect a temperature change of about 0.5° C., followed by areas around the mouth (the upper and lower hairy lip, mouth corner) and lateral chin. The mid-cheek and periauricular skin were less sensitive (able to detect a temperature change of about 2° C.), and the forearm and scalp were least sensitive (able to detect a temperature change of about 3° C.). Essick et al. did not examine the areas around the nostrils.

In an earlier study (Wei, U.S. Ser. No. 14/544,355), DIPA-1-7, the most potent compound for dynamic cooling, was tested at other topical sites on the cranium. A 20 mg/mL solution was applied, using a cotton wipe, onto the skin above the buccal cheek, the parotid-masseteric cheek, temple, and the skin above the periauricular region, and the posterior mandible using the appropriate craniometric points (pterion, coronion, condylion, and gonion, respectively) as landmarks. Surprisingly, at all of these sites, other than the buccal cheek, little cooling was observed. Mild cooling was observed on the buccal cheek for approximately 30 minutes, but this effect may have been due to the spread of the solution onto the receptive field of the infraorbital nerve. DIPA-1-7 and related analogs were, however, potently active on the eyelid margins.

To ascertain the sites and mechanisms of mask discomfort, we experimented. In South Korea, DIPA-1-7 is available as a tube of 30 g dermatological gel formulated as 1.5% wt/vol for the treatment of itch. This gel, called Intrinsic IB, was topically applied to different sites of the face of five male volunteers (aged 32 to 56). The gel was applied with a forefinger at 0.03 to 0.05 mL to discrete sites of the face normally covered by a mask: namely, 1. Alar crease. 2. External nares. 3. Lateral cheek. 4. Nasolabial folds. 5. Philtrum. 6. Vermilion, and 7. Chin, as shown in FIG. 9. The Intrinsic IB was weighed before and after each application to record the amount that was applied. Surprisingly, the rank order of sensitivity was the same for all five subjects. For coolness and cold, the rank order was alar crease>external nares≅philtrum>vermilion≅nasolabial folds>chin>>lateral cheek. The rank order is most likely determined by the TRPM8 nerve fiber density and by the thickness of the skin at the site. The number of cell layers on the cheek is about 10±3, and 7 for the nasolabial folds (Zhen et al. Number of cell layers of the stratum corneum in normal skin—relationship to the anatomical location on the body, age, sex and physical parameters. Arch Dermatol Res (1999) 291: 555-559).

The subjects were then instructed to repeat the application but this time to also use a N95 FFR for ~1 hr. Afterwards the subjects were asked what was the best site to counteract the discomfort caused by the mask. Surprisingly and unexpectedly, although all sites gave coolness and cold sensations at various intensities, the test subjects stated that only gel application on the nares prevented the development of face mask discomfort. Applications to other sites, for example, to the nasolabial folds or lips did not relieve discomfort. If there was mask discomfort the application to the skin of the nares (nostrils) was instantly effective. There was no ambiguity in the results for these five subjects. Everybody agreed that the gel on the nares prevented or counteracted the mask discomfort, and this site of application gave the best results. FIG. 5. is an illustration of the human face showing the test sites for applying a gel containing 1.5% (15 mg/mL) of DIPA-1-7. The sites are identified by the numbered circles: 1. Alar crease. 2. External nares. 3. Lateral cheek. 4. Nasolabial folds. 5. Philtrum. 6. Vermilion. 7. Chin. A 0.03 to 0.05 mL aliquot of a commercial gel containing 1.5% of DIPA1-7 (Intrinsic IB, Dong Wha Pharmaceuticals, Seoul, Republic of Korea) was applied with a forefinger to the designated site.

Further discussion with the test subjects illuminated the mechanism of drug action. They said that application on the nasolabial folds or the lips gave overt sensations of cold, but did not help much on the mask discomfort. On the other hand, the gel about the nares gave a sense of free, unimpeded cool airflow. The subjects no longer noticed that they were wearing a mask and could, for example, continue to work on the computer without annoyance. The test subjects stated that if the nose felt cold, air movement with each breath also felt fresh and cold, and the resistance to breathing disappeared. This refreshed breathing was not present if the skin only felt cold on the nasolabial folds or the chin.

In modern sensory physiology, the mechanism of action of TRPM8 agonists on mask discomfort has a distinct language. The skin of the nose, especially around the nostrils, has sensors for heat abstraction when the temperature drops to the cool range of <25° C. Activation of these "thermistors" or TRPM8 nerve endings on a cold day or the ski slope gives the subject a "runny nose." The sensors convey the pleasure of breathing cool air by the seaside or on a breezy day. The sensors shut off behind a face mask when airflow diminishes or occlude, and heat accumulates >25° C. There is no air movement. As noted earlier, in the natural state, the sensors respond best to the temperature rate change, not static temperature. That is, the brain "sees" $-\Delta°$ C./t and not absolute ° C. A TRPM8 receptor agonist, such as DIPA-1-7 or DIPA-1-9 on the skin of the nostrils, restores and enhances the thermosensitivity to coolness. The air-conditioning system re-adjusts and the subject feels better with a sense of cool airflow when breathing. The subject forgets the annoyance of the facial covering.

This result may also explain why masks are uncomfortable. Constant breathing of static warm air causes discomfort, not just heat or humidity. Refreshed breathing is a dynamic event. With a mask, the subject feels suffocated because the air does not move. With cooling, there is a relief of discomfort. Sensory physiologists know that dynamic and not static neuronal discharges into the brain account for the heat abstraction sensation of cooling in humans. Refreshing cooling is a dynamic event that requires the discharge of TRPM8 nerve fibers. DIPA compounds on the nostrils accelerate this neuronal event.

Study 5
Methods of Delivery to TRPM8 Targets and Test Results

To further characterize this discovery, a method for selective drug delivery to the skin of the nares was improvised. The hollow of the volar palm forms a receptacle that holds about 0.5 to 1 mL of liquid. This hollow is a perfect fit for the nose tip. An ideal delivery method to the nares skin is to place a solution into the hollow and immerse the nose tip into the hollow for ~5 sec. This technique allows an even distribution of drugs and comparisons of molecular potency and duration of action. For example, to construct dose-response data, a TRPM8 agonist solution was stored at a fixed volume in a disposable reservoir unit (3 mL polyethylene bottle) at 0.25 to 4 mg/mL solution in saline. Next, 0.08 mL aliquot is weighed and put onto the hollow of the palm. The nose tip is immersed into the hollow at a ~45° angle for 5 sec, as shown in FIG. 7. The tip of the nose fits snugly into the palmar cavity and precisely delivers localized test solution to the skin of the nostrils. Inhalation of the solution into the nasal cavity itself is optional but not necessary. Alternatively, one can use a gel in the hollow of the palm.

Figure 10:
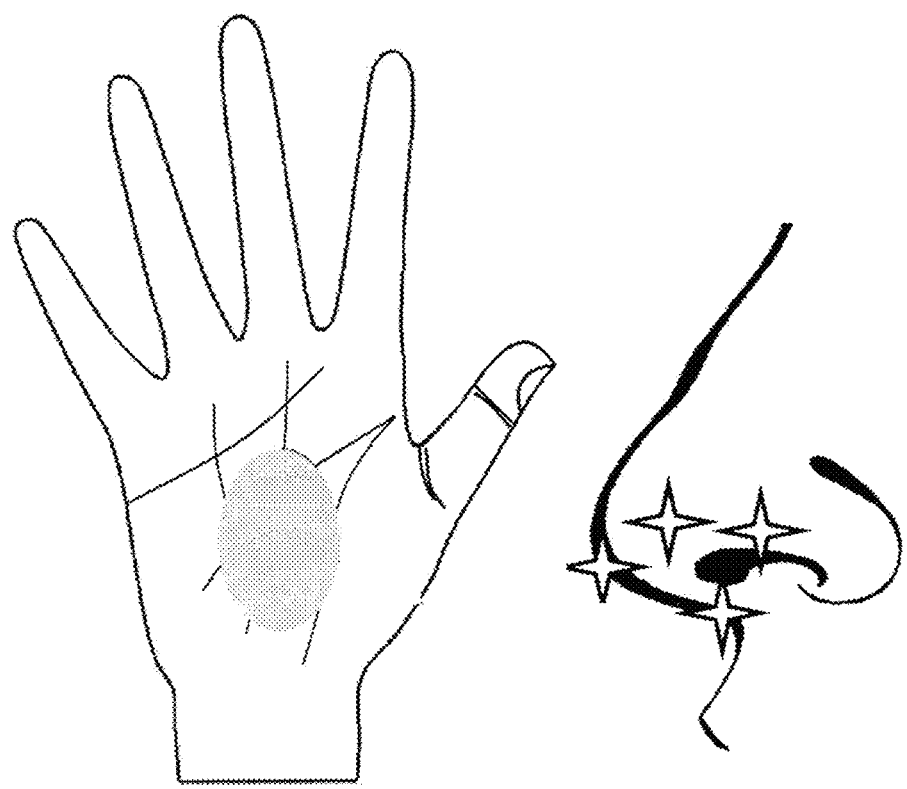
FIG. 10. is an illustration of a bioassay procedure of a cooling agent applied to the nares. A 0.8 mL volume of the test substance is placed in the hollow of the palm (gray area). The tip of the nose (at ~45° angle) was immersed into the center of the hollow for 5 sec. The contact points on the nostrils are starred.

FIG. 10. is an illustration of a bioassay procedure of a cooling agent applied to the nares. The gray area is the palm hollow. The stars on the nostrils are the contact points for the drug solution.

Figure 11:
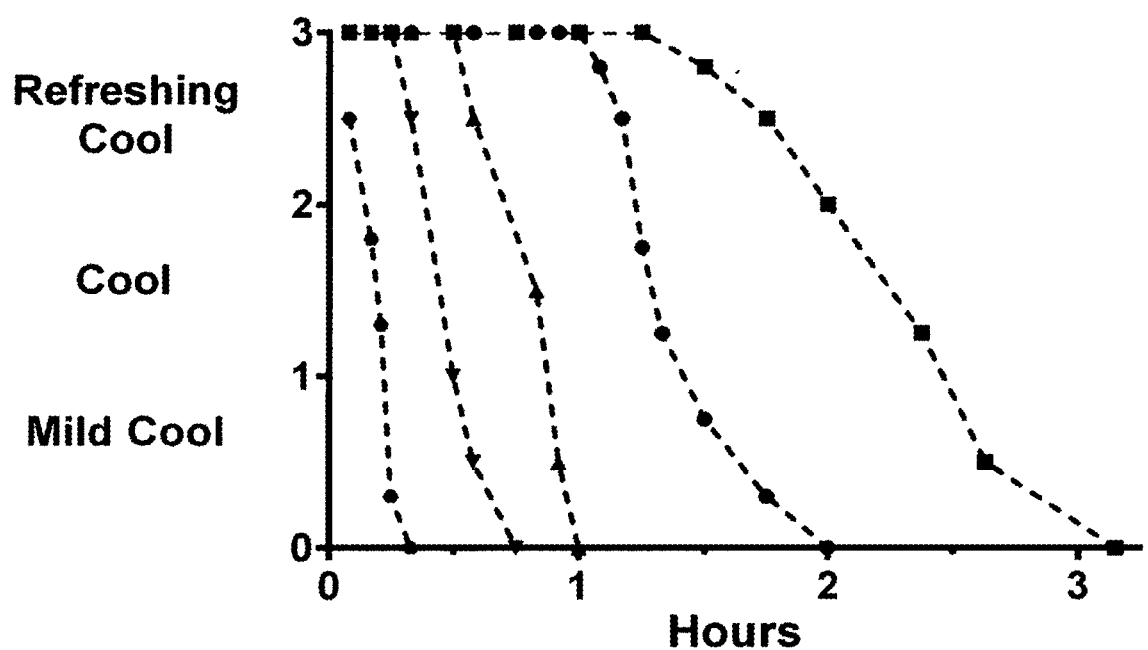
FIG. 11. is an illustration of the cooling effects of DIPA-1-9 applied to the nares using the hollow of the palm assay. Test results were for 0.25, 0.5, 1.0, 2.0 and 4.0 mg/mL of DIPA-1-9 dissolved in saline and placed at 1 mL in the hollow of the palm for immersion of the nares for ~5 sec.

Surprisingly, this method of contacting a TRPM8 agonist yielded robust dose-response data, as shown in FIG. 11. In practice, a single local application of DIPA-1-9 at 2 mg/mL in saline is sufficient to overcome mask discomfort for at least 4 hr and can be repeated with equal effect for another 4-hr period. By comparison, localized wiping of the DIPA analogs to other facial areas, such as the upper lip, philtrum, lips, and chin, were less effective for reducing mask discomfort.

FIG. 11. is an illustration of the cooling effects of DIPA-1-9 applied to the nares using the hollow of the palm assay. The results were for DIPA-1-9 at 0.25, 0.5, 1.0, 2.0, and 4.0 mg/mL dissolved in saline.

The liquid method of the delivery is good for experimental studies, but in practice a gel is more convenient. The ideal location for delivery of the gel is the "soft triangle pocket", as shown in FIG. 13. The gel is clear, translucent, and suitable for topical applications. The high-speed FlackTek centrifuge is a technical aid for mixing. Gel application is with a Puritan (Gullford, Me., USA) 803 PCL cotton-tipped applicator with an 8 cm handle. The weight of the applicator after loading was 64±3 mg (n=25 trials), and the off-loaded amount of 24±2.6 mg. On average, the off-load was 36% of the loaded volume. By varying the load, the dose can be controlled. The application can be repeated per nostril. Various compounds were tested at different concentrations and the results show in Table. The DIPA-1-7 gel at 6 mg/mL or 9 mg/mL is ideally suited for reducing face mask discomfort for ~4 hr.

Study 6
Comparison of Analogs

Screening criteria were defined to select preferred embodiments. The quality of gel applied to the nares was rated. Ideally, the gel had to be refreshing but not irritating, and last for at least 90 min. Icy cold or rhinorrhea was either present or not. The chin was a site of testing, and the gel's clarity and homogeneity were quantified. The global "effectiveness" rated on an all-or-none basis. The sum of "+" scores gave an overall picture of positive qualities.

The selection of dose and methods of formulation and testing were as:

Each chemical was formulated as a gel in Carbopol™980 NF (0.5% wt/vol in distilled water) at 1.2 mg/mL and applied to the "soft triangle pocket" or to the chin with a tipped applicator (FIG. 13). The mixing was at 3000 rpm for 5 min in a FlackTek™ Speedmixer centrifuge unit. The off-loaded volume per application was ~80 mg, to approximate a dose of 1 mg of the chemical. The coolness and duration were noted each 15 min for up to 3 hr. The parameters tested were:

1. Coolness was rated as: 0=absence of significant effect, +=present, ++=presence is obvious, and +++=refreshing and strong.
2. Duration of coolness on nostrils was rated as: 0=absence of significant effect, +=present for ≤30 min, ++=present for ≥30-90 min, and +++=present for >90 min.
3. Chin: the gel was applied to the chin. Coolness was rated as: 0=absence of significant effect, +=present for ≤30 min, ++=present for ≥0 to 90 min, and +++=present for >90 min.
4. Clarity of the gel after mixing was rated according to its transluscence to light: 0=cloudy with clumps of white crystals, +=cloudy but homogeneous, ++=partially cloudy but homogeneous, +++=clear and transparent.
5. "Effective" is a global judgment of the chemical for further development to treat mask discomfort. 0=negative, +=positive.
6. Scores is the total number of "+" ratings.
7. Icy sensations on the nose tip checked as an all-or-none event. 0=not present, +=present.
8. Rhinorrhea checked as an all-or-none event. 0=not present, +=present.

After testing, the results gave more insights into the criteria for the selection of an agent for mask discomfort (Table 8). For short-term use, for example, for surgical mask discomfort, an agent such as 2-5, 1-5, and 1-6 are adequate for treatment. For longer-term use, however, e.g., for work with patients with respiratory infections, ideal agents are 1-7 or 1-8. Individual chemicals have unique attributes: for example, DIPA-1-9 produced a sustained, long-acting, mild cooling, which was very comfortable. 2-5 gave an immediate, robust, and refreshing cooling sensation. For short-term relief, 2-5 has sufficient activity to be the right candidate. The 2-6 and 3,4-6 entities lacked sufficient duration of action. The 1-10 analog simply did not work.

The 2-5, 2-6, 3,4-6, and 3,4-7 molecules are chiral and have at least four enantiomers. Separating the enantiomers may identify more potent and selective agonists.

TABLE 8

1-Dialkylphosphorylalkane gel tests on soft triangle pocket or chin of a volunteer. Chemical structures are shown in Tables 1-3.

| Chemical | Coolness | Duration | Chin | Clarity Gel | Effective | Score | Icy | Rhinorrhea |
|---|---|---|---|---|---|---|---|---|
| 1-5 | +++ | ++ | ++ | +++ | ✓ | 10 | ✓ | ✓ |
| 1-6 | +++ | +++ | +++ | +++ | ✓ | 12 | ✓ | ✓ |
| 1-7 | +++ | +++ | +++ | +++ | ✓ | 12 | ✓ | ✓ |
| 1-8 | +++ | +++ | +++ | +++ | ✓ | 12 | 0 | 0 |
| 1-9 | ++ | +++ | + | ++ | ✓ | 8 | 0 | 0 |
| 1-10 | 0 | 0 | 0 | + | 0 | 0 | 0 | 0 |
| 2-5 | +++ | + | + | +++ | ✓ | 8 | 0 | 0 |
| 2-6 | ++ | + | + | + | ✓ | 5 | 0 | 0 |
| 3, 4-6 | ++ | + | + | ++ | 0 | 6 | 0 | 0 |
| 3, 4-7 | +++ | ++ | + | + | ✓ | 7 | 0 | 0 |

In summary, an essential part of this discovery is the recognition that skin at the opening of the nostrils is highly sensitive to thermal stimuli and influences airflow comfort and discomfort. Wearing a mask becomes uncomfortable when the ambient environment is >25° C. The second part of the discovery is the identification of selective TRPM8 agonist molecules that can be precisely delivered to the nostril site to relieve mask discomfort. The prior art does not record this method of selective topical delivery of a cooling agent to the nares skin and nasal vestibule skin for the treatment of mask discomfort.

REFERENCES

Publications are cited herein to more fully describe and disclose the discovery and the state of the art to which the discovery pertains. Each of these publications is incorporated herein by reference in its entirety into the present disclosure.

The invention claimed is:

1. A method for reducing sensory discomfort caused by wearing a face mask for more than one hour, the method comprising:
   (1) topically applying a liquid or semi-liquid composition to the skin of the subject's nares, the composition comprising a carrier and a therapeutically effective amount of a compound having Formula 1

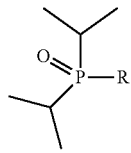

Formula 1 wherein R is n-pentyl, n-hexyl, n-heptyl, n-octyl, or n-nonyl; and wherein the compound having Formula 1, following topical application of the composition, penetrates the skin of the subject's nares; and (2) thereafter, wearing the face mask for more than one hour, whereby the face mask covers the subject's mouth and nostrils.

2. The method as in claim 1 wherein the face mask is a surgical mask, medical mask, or a procedure mask.

3. The method as in claim 1 wherein the face mask is a N95 respirator or a similar respirator.

4. The method as in claim 1 wherein the face mask is an elastomeric respirator made of synthetic or natural rubber material.

5. The method as in claim 1 wherein the carrier is water or an isotonic saline solution.

6. The method as in claim 1 wherein the liquid or semi-liquid composition is a rinse and has from about 0.01 to 0.025% by weight of the Formula 1 compound.

7. The method as in claim 1 wherein the liquid or semi-liquid composition is a gel or a cream.

8. The method as in claim 7 wherein the liquid or semi-liquid composition further comprises a carbomer.

9. The method as in claim 1 wherein the liquid or semi-liquid composition has from about 0.05 to 5% by weight of the Formula 1 compound.

10. The method as in claim 1 wherein the Formula 1 compound is 1-diisopropyl-phosphinoyl-pentane [DIPA-1-5], 1-diisopropyl-phosphinoyl-hexane [DIPA-1-6], 1-diisopropyl-phosphinoyl-heptane [DIPA-1-7], 1-diisopropyl-phosphinoyl-octane [DIPA-1-8], or 1-diisopropyl-phosphinoyl-nonane [DIPA-1-9] and the therapeutically effective amount is from about 1 to 5 mg.

11. The method as in claim 8 wherein the Formula 1 compound is selected from the group consisting of 1-diisopropyl-phosphinoyl-pentane [DIPA-1-5], 1-diisopropyl-phosphinoyl-hexane [DTPA-1-6], 1-iisopropyl-phosphinoyl-heptane [DTPA-1-7], 1-diisopropyl-phosphinoyl-octane [DIPA-1-8], 1-diisopropyl-phosphinoyl-nonane [DTPA-1-9], and mixtures thereof, and the therapeutically effective amount is from about 1 to 5 mg.

* * * * *